(12) United States Patent
von Oepen et al.

(10) Patent No.: US 11,109,967 B2
(45) Date of Patent: Sep. 7, 2021

(54) SYSTEMS AND METHODS FOR LOADING AND DEPLOYING AN INTRAVASCULAR DEVICE

(71) Applicant: Cephea Valve Technologies, Inc., Santa Clara, CA (US)

(72) Inventors: Randolf von Oepen, Aptos, CA (US); Sean A. McNiven, Menlo Park, CA (US); Francisco Valencia, East Palo Alto, CA (US); Ken C. Salvador, Hayward, CA (US); Yongjin Xie, Cupertino, CA (US)

(73) Assignee: CEPHEA VALVE TECHNOLOGIES, INC., Santa Clara, CA (US)

( * ) Notice: Subject to any disclaimer, the term of this patent is extended or adjusted under 35 U.S.C. 154(b) by 255 days.

(21) Appl. No.: 15/662,089

(22) Filed: Jul. 27, 2017

(65) Prior Publication Data

US 2018/0055637 A1    Mar. 1, 2018

Related U.S. Application Data

(60) Provisional application No. 62/380,795, filed on Aug. 29, 2016, provisional application No. 62/430,149, (Continued)

(51) Int. Cl.
*A61F 2/24*    (2006.01)
*A61B 17/00*    (2006.01)
(Continued)

(52) U.S. Cl.
CPC ...... *A61F 2/2436* (2013.01); *A61B 17/00234* (2013.01); *A61B 17/1285* (2013.01);
(Continued)

(58) Field of Classification Search
CPC ........ A61F 2/2436; A61F 2/2427; A61F 2/24; A61F 2002/9522; A61M 25/0147; A61B 2017/00867; A61B 2017/00323
See application file for complete search history.

(56) References Cited

U.S. PATENT DOCUMENTS 4,406,656 A    9/1983 Hattler et al.
4,728,319 A    3/1988 Masch
(Continued)

FOREIGN PATENT DOCUMENTS

CN    1469724    1/2004
CN    1688352 A    10/2005
(Continued)

OTHER PUBLICATIONS

Takizawa H et al: "Development of a microfine active bending catheter equipped with MIF tactile sensors", Micro Electro Mechanical Systems, 1999. MEMS '99. Twelfth IEEE International Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3.
(Continued)

*Primary Examiner* — Anh T Dang
(74) *Attorney, Agent, or Firm* — Workman Nydegger

(57) ABSTRACT

An intravascular device delivery system includes an elongated member with a distal end cap and a delivery disc that are longitudinally movable using a disc handle. A main body of the disc handle is configured to move the distal end cap and a movable body of the disc handle is configured to move the delivery disc. The movable body is movable relative to the main body, and the main body and movable body are movable together.

25 Claims, 14 Drawing Sheets

Related U.S. Application Data filed on Dec. 5, 2016, provisional application No. 62/436,985, filed on Dec. 20, 2016.

(51) Int. Cl.

| | |
|---|---|
| *A61B 17/128* | (2006.01) |
| *A61M 25/00* | (2006.01) |
| *A61M 25/01* | (2006.01) |
| *A61M 25/06* | (2006.01) |
| *A61M 25/09* | (2006.01) |
| *A61F 2/95* | (2013.01) |
| *A61B 17/122* | (2006.01) |

(52) U.S. Cl.
CPC ....... *A61F 2/2427* (2013.01); *A61M 25/0045* (2013.01); *A61M 25/0136* (2013.01); *A61M 25/0147* (2013.01); *A61M 25/0662* (2013.01); *A61M 25/09* (2013.01); *A61B 17/122* (2013.01); *A61B 2017/00243* (2013.01); *A61B 2017/00323* (2013.01); *A61B 2017/00867* (2013.01); *A61F 2/9517* (2020.05); *A61F 2/9522* (2020.05); *A61F 2210/0014* (2013.01); *A61M 2025/0046* (2013.01)

(56) References Cited

U.S. PATENT DOCUMENTS

| | | |
|---|---|---|
| 5,053,043 A | 10/1991 | Gottesman et al. |
| 5,059,213 A | 10/1991 | Chesterfield et al. |
| 5,078,722 A | 1/1992 | Stevens |
| 5,078,723 A | 1/1992 | Dance et al. |
| 5,236,450 A | 8/1993 | Scott |
| 5,325,845 A | 7/1994 | Adair |
| 5,345,945 A | 9/1994 | Hodgson et al. |
| 5,387,219 A | 2/1995 | Rappe |
| 5,415,664 A | 5/1995 | Pinchuk |
| 5,472,423 A | 12/1995 | Gronauer |
| 5,571,085 A | 11/1996 | Accisano, III |
| 5,662,606 A | 9/1997 | Cimino et al. |
| 5,669,919 A | 9/1997 | Sanders et al. |
| 5,769,812 A | 6/1998 | Stevens et al. |
| 5,807,405 A | 9/1998 | Vanney et al. |
| 5,820,591 A | 10/1998 | Thompson et al. |
| 5,843,103 A | 12/1998 | Wulfman |
| 5,855,601 A | 1/1999 | Bessler et al. |
| 5,873,882 A | 2/1999 | Straub et al. |
| 5,902,334 A | 5/1999 | Dwyer et al. |
| 5,906,642 A | 5/1999 | Caudillo et al. |
| 5,957,973 A | 9/1999 | Quiachon et al. |
| 6,090,118 A | 7/2000 | McG Uckin, Jr. |
| 6,180,059 B1 | 1/2001 | Divino, Jr. et al. |
| 6,228,110 B1 | 5/2001 | Munsinger |
| 6,458,137 B1 | 10/2002 | Klint |
| 6,517,550 B1 | 2/2003 | Konya et al. |
| 6,695,836 B1 | 2/2004 | DeMello et al. |
| 6,926,725 B2 | 8/2005 | Cooke et al. |
| 7,172,617 B2 | 2/2007 | Colgan et al. |
| 7,344,553 B2 | 3/2008 | Opolski et al. |
| 7,666,204 B2 | 2/2010 | Thornton et al. |
| 7,736,388 B2 | 6/2010 | Goldfarb et al. |
| 7,837,727 B2 | 11/2010 | Goetz et al. |
| 7,988,724 B2 | 8/2011 | Salahieh et al. |
| 7,993,303 B2 | 8/2011 | Von Oepen et al. |
| 8,157,852 B2 | 4/2012 | Bloom et al. |
| 8,523,881 B2 | 9/2013 | Cabiri et al. |
| 8,647,323 B2 | 2/2014 | Guo et al. |
| 8,911,455 B2 * | 12/2014 | Quadri ................ A61F 2/2439 606/139 |
| 8,926,588 B2 | 1/2015 | Berthiaume et al. |
| 8,926,692 B2 | 1/2015 | Dwork |
| 9,339,378 B2 | 5/2016 | Quadri et al. |
| 9,370,423 B2 | 6/2016 | Ryan |
| 9,393,112 B2 | 7/2016 | Tuval et al. |
| 9,399,112 B2 | 7/2016 | Shevgoor et al. |
| 9,668,859 B2 | 6/2017 | Kheradvar et al. |
| 9,687,373 B2 | 6/2017 | Vad |
| 9,693,862 B2 | 7/2017 | Campbell et al. |
| 9,801,745 B2 | 10/2017 | Wubbeling et al. |
| 10,111,671 B2 | 10/2018 | Bodewadt |
| 10,117,760 B2 | 11/2018 | Mangiardi |
| 10,376,673 B2 | 8/2019 | Van Hoven et al. |
| 10,398,553 B2 | 9/2019 | Kizuka |
| 10,470,902 B2 | 11/2019 | Sheldon et al. |
| 10,661,052 B2 | 5/2020 | McNiven et al. |
| 2001/0002445 A1 | 5/2001 | Vesely |
| 2001/0047150 A1 | 11/2001 | Chobotov |
| 2002/0013547 A1 | 1/2002 | Paskar |
| 2004/0049207 A1 | 3/2004 | Goldfarb et al. |
| 2004/0064179 A1 | 4/2004 | Linder et al. |
| 2004/0116848 A1 | 6/2004 | Gardeski et al. |
| 2004/0127849 A1 | 7/2004 | Kantor |
| 2004/0133232 A1 | 7/2004 | Rosenbluth et al. |
| 2004/0147826 A1 | 7/2004 | Peterson |
| 2005/0038383 A1 | 2/2005 | Kelley et al. |
| 2005/0085903 A1 | 4/2005 | Lau |
| 2005/0137695 A1 | 6/2005 | Salahieh et al. |
| 2005/0143809 A1 | 6/2005 | Salahieh et al. |
| 2005/0256452 A1 | 11/2005 | DeMarchi et al. |
| 2005/0259452 A1 | 11/2005 | Cho |
| 2005/0283231 A1 | 11/2005 | Haug et al. |
| 2005/0277874 A1 | 12/2005 | Selkee |
| 2005/0277876 A1 | 12/2005 | Hayden |
| 2005/0288768 A1 | 12/2005 | Sowinski et al. |
| 2006/0135961 A1 | 6/2006 | Rosenman et al. |
| 2007/0060997 A1 | 3/2007 | de Boer |
| 2007/0156225 A1 | 7/2007 | George et al. |
| 2007/0173757 A1 | 7/2007 | Levine et al. |
| 2007/0197858 A1 | 8/2007 | Goldfarb et al. |
| 2007/0203561 A1 | 8/2007 | Forster et al. |
| 2007/0260225 A1 | 11/2007 | Sakakine et al. |
| 2007/0270779 A1* | 11/2007 | Jacobs .............. A61M 25/0045 604/525 |
| 2007/0299424 A1 | 12/2007 | Cumming et al. |
| 2008/0103585 A1 | 5/2008 | Monstadt et al. |
| 2008/0109065 A1 | 5/2008 | Bowe |
| 2008/0188850 A1 | 8/2008 | Mody et al. |
| 2008/0195126 A1 | 8/2008 | Solem |
| 2009/0036768 A1 | 2/2009 | Seehusen et al. |
| 2009/0069885 A1 | 3/2009 | Randert et al. |
| 2009/0099554 A1 | 4/2009 | Forster et al. |
| 2009/0163934 A1 | 6/2009 | Raschdorf, Jr. et al. |
| 2009/0182407 A1 | 7/2009 | Leanna et al. |
| 2009/0204005 A1 | 8/2009 | Keast et al. |
| 2009/0240326 A1 | 9/2009 | Wilson et al. |
| 2009/0276039 A1 | 11/2009 | Meretei |
| 2009/0281619 A1 | 11/2009 | Le et al. |
| 2010/0004739 A1 | 1/2010 | Vesely |
| 2010/0044410 A1 | 2/2010 | Argentine et al. |
| 2010/0059173 A1 | 3/2010 | Kampa et al. |
| 2010/0070009 A1 | 3/2010 | Barker |
| 2010/0217261 A1 | 8/2010 | Watson |
| 2010/0249894 A1 | 9/2010 | Oba et al. |
| 2010/0331776 A1 | 12/2010 | Salahieh et al. |
| 2011/0112630 A1 | 5/2011 | Groothuis et al. |
| 2011/0166566 A1 | 7/2011 | Gabriel |
| 2011/0166649 A1 | 7/2011 | Gross et al. |
| 2011/0202128 A1 | 8/2011 | Duffy |
| 2011/0257718 A1* | 10/2011 | Argentine ............... A61F 2/966 623/1.11 |
| 2011/0307049 A1 | 12/2011 | Kao |
| 2012/0022640 A1 | 1/2012 | Gross et al. |
| 2012/0065464 A1 | 3/2012 | Elllis et al. |
| 2012/0109078 A1 | 5/2012 | Schaeffer |
| 2012/0172915 A1 | 7/2012 | Fifer et al. |
| 2012/0316639 A1 | 12/2012 | Kleinschrodt |
| 2012/0330348 A1 | 12/2012 | Strauss et al. |
| 2012/0330408 A1 | 12/2012 | Hillukka et al. |
| 2013/0030514 A1 | 1/2013 | Kasprzak et al. |
| 2013/0041314 A1 | 2/2013 | Dillon |
| 2013/0066342 A1 | 3/2013 | Dell et al. |
| 2013/0103001 A1 | 4/2013 | BenMaamer et al. |
| 2013/0109910 A1 | 5/2013 | Alexander et al. |

(56) References Cited

U.S. PATENT DOCUMENTS

| | | | |
|---|---|---|---|
| 2013/0131775 A1* | 5/2013 | Hadley | A61F 2/966 623/1.11 |
| 2013/0289696 A1 | 10/2013 | Maggard et al. | |
| 2014/0107693 A1 | 4/2014 | Plassman | |
| 2014/0114390 A1 | 4/2014 | Tobis et al. | |
| 2014/0142688 A1 | 5/2014 | Duffy et al. | |
| 2014/0148889 A1 | 5/2014 | Deshmukh et al. | |
| 2014/0180124 A1 | 6/2014 | Whiseant et al. | |
| 2014/0200649 A1* | 7/2014 | Essinger | A61F 2/9517 623/1.12 |
| 2014/0228871 A1 | 8/2014 | Cohen et al. | |
| 2014/0276966 A1 | 9/2014 | Ranucci et al. | |
| 2014/0324164 A1 | 10/2014 | Gross et al. | |
| 2014/0336744 A1 | 11/2014 | Tani et al. | |
| 2014/0379074 A1 | 12/2014 | Spence et al. | |
| 2015/0005704 A1 | 1/2015 | Heisel et al. | |
| 2015/0005801 A1 | 1/2015 | Marquis et al. | |
| 2015/0088189 A1 | 3/2015 | Paul, Jr. | |
| 2015/0112430 A1 | 4/2015 | Creaven et al. | |
| 2015/0272759 A1 | 10/2015 | Argentine | |
| 2015/0306806 A1 | 10/2015 | Dando et al. | |
| 2016/0045311 A1 | 2/2016 | McCann et al. | |
| 2016/0074163 A1 | 3/2016 | Yang et al. | |
| 2016/0113765 A1 | 4/2016 | Ganesan et al. | |
| 2016/0143661 A1 | 5/2016 | Wood et al. | |
| 2017/0035566 A1 | 2/2017 | Krone et al. | |
| 2017/0042678 A1 | 2/2017 | Ganesan et al. | |
| 2017/0080186 A1 | 3/2017 | Salahieh et al. | |
| 2017/0232238 A1 | 8/2017 | Biller et al. | |
| 2018/0028177 A1 | 2/2018 | von Oepen et al. | |
| 2018/0028215 A1 | 2/2018 | Cohen | |
| 2018/0028305 A1 | 2/2018 | von Oepen et al. | |
| 2018/0028779 A1 | 2/2018 | von Oepen et al. | |
| 2018/0028787 A1 | 2/2018 | McNiven et al. | |
| 2018/0055636 A1 | 3/2018 | Valencia et al. | |
| 2018/0056033 A1 | 3/2018 | von Oepen et al. | |
| 2018/0056043 A1 | 3/2018 | von Oepen et al. | |
| 2018/0071098 A1 | 3/2018 | Alon | |
| 2018/0092744 A1 | 4/2018 | von Oepen et al. | |
| 2018/0126119 A1 | 5/2018 | McNiven et al. | |
| 2018/0132837 A1 | 5/2018 | Mathena et al. | |
| 2018/0133454 A1 | 5/2018 | von Oepen et al. | |
| 2018/0360457 A1 | 12/2018 | Ellis et al. | |
| 2019/0030285 A1 | 1/2019 | Prabhu et al. | |
| 2019/0274831 A1 | 9/2019 | Prabhu | |
| 2020/0155804 A1 | 5/2020 | von Oepen et al. | |
| 2020/0230352 A1 | 7/2020 | McNiven et al. | |
| 2020/0230354 A1 | 7/2020 | Von Oepen et al. | |

FOREIGN PATENT DOCUMENTS

| | | |
|---|---|---|
| CN | 1961983 A | 5/2007 |
| CN | 101247847 A | 8/2008 |
| CN | 101426452 A | 5/2009 |
| CN | 101479006 A | 7/2009 |
| CN | 101506538 A | 8/2009 |
| CN | 102159277 A | 8/2011 |
| CN | 102258402 A | 11/2011 |
| CN | 102405022 A | 4/2012 |
| CN | 102481433 A | 5/2012 |
| CN | 102548505 A | 7/2012 |
| CN | 102770080 | 11/2012 |
| CN | 102933161 A | 2/2013 |
| CN | 103517689 A | 1/2014 |
| CN | 103702635 A | 4/2014 |
| CN | 103841899 | 6/2014 |
| CN | 103957993 A | 7/2014 |
| CN | 104203329 A | 12/2014 |
| CN | 104812439 A | 7/2015 |
| CN | 105246434 A | 1/2016 |
| CN | 105899167 A | 8/2016 |
| EP | 0989882 A1 | 4/2000 |
| EP | 1980288 | 10/2008 |
| EP | 2537487 | 12/2012 |
| EP | 2702965 | 3/2014 |
| EP | 3009103 | 4/2016 |
| JP | 2003062072 | 3/2003 |
| JP | 2006528911 | 12/2006 |
| JP | 2013516244 | 5/2013 |
| WO | WO 2001051114 | 7/2001 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2012020521 | 2/2012 |
| WO | 2012/057983 A1 | 5/2012 |
| WO | WO 2012151396 | 11/2012 |
| WO | 2013/126529 A2 | 8/2013 |
| WO | WO 2014064694 | 5/2014 |
| WO | WO 2014121280 | 8/2014 |
| WO | WO 2014128705 | 8/2014 |
| WO | WO 2015191938 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | WO 2016183526 | 11/2016 |
| WO | 2017/023534 A2 | 2/2017 |
| WO | WO 2018023038 | 2/2018 |
| WO | WO 2018023043 | 2/2018 |
| WO | WO 2018023044 | 2/2018 |
| WO | WO 2018023045 | 2/2018 |
| WO | WO 2018023052 | 2/2018 |
| WO | WO 2018044446 | 3/2018 |
| WO | WO 2018044447 | 3/2018 |
| WO | WO 2018044448 | 3/2018 |
| WO | WO 2018044449 | 3/2018 |
| WO | WO 2018067788 | 4/2018 |
| WO | WO 2018093426 | 5/2018 |

OTHER PUBLICATIONS

U.S. Appl. No. 15/662,013, Jun. 13, 2019, Office Action.
U.S. Appl. No. 15/662,013, Oct. 10, 2019, Office Action.
U.S. Appl. No. 15/662,066, Feb. 27, 2020, Advisory Action.
U.S. Appl. No. 15/662,076, Jan. 31, 2020, Notice of Allowance.
U.S. Appl. No. 15/662,008, Jan. 31, 2020, Notice of Allowance.
U.S. Appl. No. 15/662,098, Jan. 27, 2020, Office Action.
U.S. Appl. No. 15/662,142, Apr. 17, 2020, Office Action.
U.S. Appl. No. 15/662,001, Mar. 24, 2020, Notice of Allowance.
U.S. Appl. No. 15/662,098, Mar. 23, 2020, Advisory Action.
U.S. Appl. No. 15/724,499, Mar. 25, 2020, Office Action.
U.S. Appl. No. 15/662,001, Jun. 20, 2019, Office Action.
U.S. Appl. No. 15/662,001, Oct. 4, 2019, Office Action.
U.S. Appl. No. 15/662,001, Dec. 18, 2019, Notice of Allowance.
U.S. Appl. No. 15/662,013, Dec. 5, 2019, Advisory Action.
U.S. Appl. No. 15/662,066, Jul. 11, 2019, Office Action.
U.S. Appl. No. 15/662,066, Dec. 16, 2019, Office Action.
U.S. Appl. No. 15/662,142, Dec. 20, 2019, Advisory Action.
U.S. Appl. No. 15/662,076, Oct. 8, 2019, Notice of Allowance.
U.S. Appl. No. 15/662,093, Mar. 7, 2019, Office Action.
U.S. Appl. No. 15/662,093, Aug. 29, 2019, Office Action.
U.S. Appl. No. 15/662,093, Dec. 3, 2019, Office Action.
U.S. Appl. No. 15/662,008, Sep. 13, 2019, Office Action.
U.S. Appl. No. 15/662,014, May 31, 2019, Office Action.
U.S. Appl. No. 15/662,014, Oct. 2, 2019, Notice of Allowance.
U.S. Appl. No. 15/662,098, Jul. 5, 2019, Office Action.
U.S. Appl. No. 15/724,499, Jul. 15, 2019, Notice of Allowance.
U.S. Appl. No. 15/724,499, Aug. 27, 2019, Notice of Allowance.
U.S. Appl. No. 15/724,499, Nov. 22, 2019, Notice of Allowance.
U.S. Appl. No. 15/662,013, May 7, 2020, Notice of Allowance.
U.S. Appl. No. 15/662,093, May 6, 2020, Office Action.
U.S. Appl. No. 15/662,098, Apr. 30, 2020, Office Action.
Advisory Action received for U.S. Appl. No. 15/662,093, dated Jul. 9, 2020.
Notice of Allowance received for U.S. Appl. No. 15/724,499, dated Jul. 1, 2020.

(56) References Cited

OTHER PUBLICATIONS

U.S. Appl. No. 15/662,066, May 21, 2020, Office Action.

* cited by examiner

SYSTEMS AND METHODS FOR LOADING AND DEPLOYING AN INTRAVASCULAR DEVICE

CROSS-REFERENCE TO RELATED APPLICATIONS

This application claims the benefit of and priority to U.S. Provisional Patent Application Ser. No. 62/380,795 filed on Aug. 29, 2016 and entitled "Systems and Methods for Loading and Deploying an Intravascular Device" and to U.S. Provisional Patent Application Ser. No. 62/430,149 filed on Dec. 5, 2016 and entitled "Systems and Methods for Loading and Deploying an Intravascular Device," which applications are expressly incorporated herein by reference in their entirety.

This application also claims the benefit of and priority to U.S. Provisional Patent Application Ser. No. 62/436,985 filed on Dec. 20, 2016 and entitled "Systems and Methods for Loading and Deploying an Intravascular Device."

BACKGROUND OF THE INVENTION

1. The Field of the Invention

The present invention generally relates to devices for moving a number of nested sheaths and structures relative to one another, and more specifically moving sheaths and structures during a medical procedure.

2. The Relevant Technology

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by tension cable, or other mechanisms positioned inside the catheter. Precise control of the distal end of the catheter allows for more reliable and faster positioning of a medical device and/or implant and other improvements in the procedures.

An intravascularly delivered device needs to be placed precisely to ensure a correct positioning of the medical device, which is essential for its functionality, as the device may be difficult to reposition after the device is fully deployed from the delivery system. Additionally, the ability to recapture a partially deployed device is desirable in the event that the distal end of the catheter moves relative to the target location and compromises the precise positioning of the device.

The expansion and/or recapture of the device requires the collapse of one or more movable or deformable portions of the device. The one or more movable or deformable portions expand and/or collapse toward the longitudinal axis of a sheath during longitudinal movement of the sheath over the transverse exterior of the device. Proximal movement of the sheath relative to the device allows the device to expand beyond a diameter of the sheath. Distal movement of the sheath relative to the device constrains the device in the tip of the sheath. More rigid and/or robust devices with a high outwards force require a stiffer sheath and/or greater longitudinal forces to move the sheath relative to the device. Increasing the stiffness of the sheath is undesirable during intravascular procedures since a stiff device might not be able to be delivered through a tortuous anatomy.

BRIEF SUMMARY

In an embodiment, an intravascular device delivery system includes an elongated member, and a disc handle. The elongated member has a distal end and a proximal end with a longitudinal axis extending therebetween. The elongated member includes an outer sleeve, at least one steerable catheter; a coil positioned longitudinally overlapping and radially within at least a portion of the outer sleeve, a distal end cap longitudinally fixed to the coil, a delivery catheter positioned longitudinally overlapping and radially within at least a portion of the coil, and a delivery disc longitudinally fixed to the delivery catheter and positioned within the coil. The disc handle is configured to move the distal end cap and delivery disc. The disc handle includes a main body configured to move the distal end cap longitudinally a movable body configured to move the delivery disc longitudinally relative to the distal end cap. In some embodiments, the delivery system can also include a flexible outer cover and one or more swivel connections between different portions of the delivery system.

In another embodiment, the system may include a loading assembly. The loading assembly can include a reservoir for holding an ice/water bath that can be used to reduce the forces needed to load an intravascular device into the distal end of the delivery system by lower the temperature of the intravascular device below its martensite transformation temperature. The loading fixture can also include a clamping assembly for selectively and securely holding the distal end of the delivery system during loading of the intravascular device.

Other embodiments may include a control fixture located at the proximal end of the delivery system. The control fixture can be connected to the proximal ends of, and can be used to selectively control relative movement of, the various component layers of a delivery catheter of the delivery system.

Various methods of loading an intravascular device into a delivery system, and various methods of deploying an intravascular device at a target site are also disclosed.

This summary is provided to introduce a selection of concepts that are further described below in the detailed description. This summary is not intended to identify specific features of the claimed subject matter, nor is it intended to be used as an aid in limiting the scope of the claimed subject matter.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
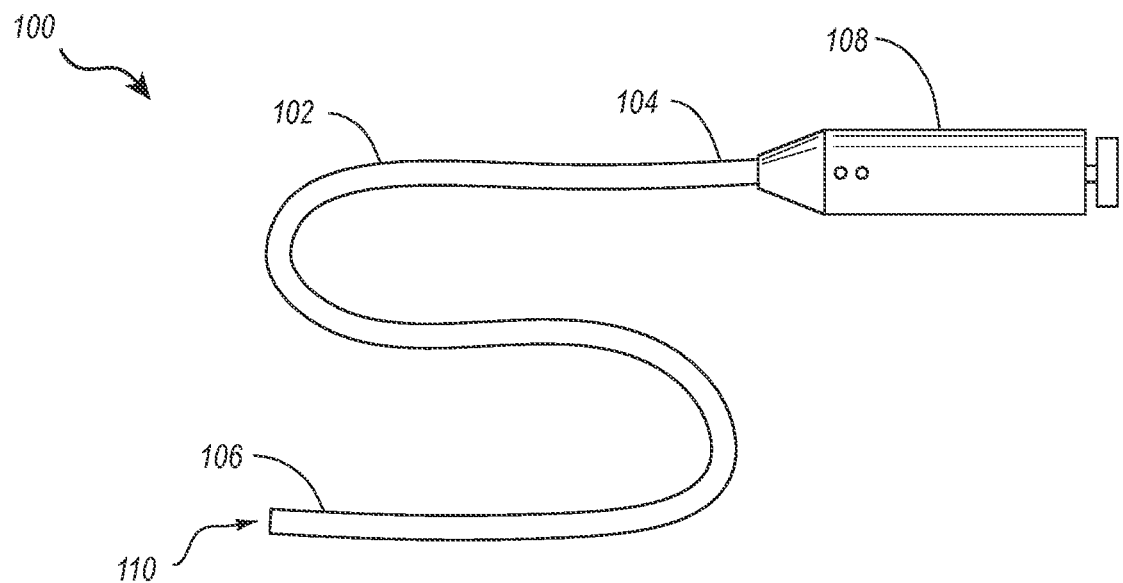
FIG. 1 is a schematic view of an embodiment of an intravascular device delivery system, according to the present disclosure.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using intravascular device delivery systems or other steerable intravascular systems. An intravascular device delivery system may allow a medical professional to deliver an intravascular or other medical device to a target location in a patient's body. While the present disclosure will describe intravascular device delivery systems and applications thereof in relation to intravascular procedures in the heart, it should be understood that the devices, systems, and method described herein may be applicable to other bodily lumens and/or cavities. Additionally, elements described in relation to any embodiment depicted and/or described herein may be combinable with elements described in relation to any other embodiment depicted and/or described herein.

An intravascular device delivery system may include a flexible elongated member that has a distal end and a proximal end. One or more handles may be connected to a proximal end of the elongated member to allow a user, such as a medical professional and/or clinician, to control one or more movements of the elongated member. An intravascular device may be positioned at and/or connected to the distal end of the elongated member.

In some embodiments, the elongated member may include a plurality of elements. For example, the elongated member may include a plurality of elements that extend from the proximal end to the distal end. In some embodiments, at least one of the elements of the elongated member may be located radially within a delivery sheath of the elongated member. In at least one embodiment, at least one element of the elongated member is located coaxially within a delivery sheath.

In some embodiments, the handle(s) may include one or more controls (e.g., a knob, a button, a lever, or other controls) that may move at least one part of the intravascular device delivery system relative to another. For example, the handle(s) may include one or more controls for moving a delivery sheath of the elongated member relative to a delivery catheter or other element of the elongated member. The handle may move the delivery sheath relative to another element of the elongated member in a proximal direction, in a distal direction, in a rotational direction, or combinations thereof.

FIG. 1 illustrates a schematic representation of an intravascular device delivery system 100. The system 100 may include an elongated member 102 having a proximal end 104 and a distal end 106. A handle 108 may be connected to the proximal end 104 of the elongated member 102. An intravascular device 110 may be positioned at and/or connected to the distal end 106 and constrained by the elongated member 102.

The elongated member 102 may be flexible in parts, stiff in other parts, allowing the elongated member 102 to traverse a patient's tortuous vasculature or other anatomy. In some embodiments, the elongated member 102 may deliver the intravascular device 110 to a target location in the patient's body, such as delivering a replacement heart valve to the heart. In other embodiments, the system 100 and elongated member 102 may be provided without an intravascular device 110 at the distal end 106 such that the system may recapture, reposition, or otherwise move an intravascular device previously positioned in the patient's body. Furthermore the system 100 might be used to perform other functions as for example being used as a positioning system to have a separate element crossing the septum wall between the right and the left atrium of a patient's heart.

The elongated member 102 of the system 100 may include one or more elements therein. An element of the elongated member 102 may include one or more deflecting catheters, elements to provide torque control, catheters or elements connecting the therapeutic device to the catheter or to the handle(s) 108, a guidewire, a guidewire lumen 122, a longitudinally movable or fixed sheath, other tubular and/or solid element, or combinations thereof. In some embodiments, an element of the elongated member 102 may extend an entire length of the elongated member 102 from a proximal end to a distal end of the elongated member 102. In other embodiments, an element of the elongated member 102 may have a length less than the entire length of the elongated member. For example, an element may provide support to the elongated member 102 from the proximal end 104 toward the distal end 106 without continuing the entire length to the distal end 106.

Figure 2:
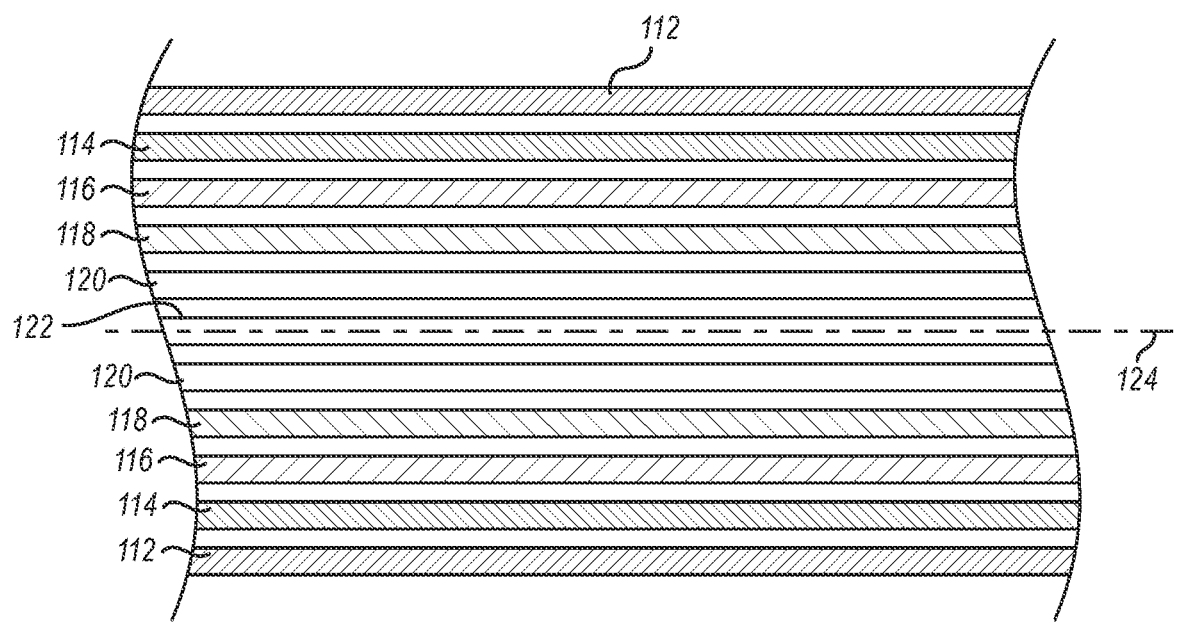
FIG. 2 is a side cross-sectional view of a portion of an embodiment of the elongated member of FIG. 1, according to the present disclosure.

FIG. 2 is a side cutaway view of an embodiment of an elongated member 102 having a plurality of elements positioned concentrically within one another. For example, an elongated member 102 may have delivery sheath 112 with one or more elements positioned radially within the delivery sheath 112. In some embodiments, the delivery sheath 112 may be an outermost element of the elongated member 102. In other embodiments, at least part of the delivery sheath 112 may be within an outermost element of the elongated member 102.

In some embodiments, an elongated member 102 may have a steerable guide catheter 114 positioned radially within the delivery sheath 112. For example, at least a portion of the steerable guide catheter 114 may longitudinally overlap with a portion of the delivery sheath 112 and the steerable guide catheter 114 may be within a lumen or other cavity of the delivery sheath 112. In other embodiments, the delivery sheath 112 may have a plurality of elements positioned radially within the delivery sheath 112. For example, the steerable guide catheter 114 and an inner steerable catheter 116 may be positioned radially within the delivery sheath 112. For example, both the steerable guide catheter 114 and inner steerable catheter 116 may be radially within the delivery sheath 112 and radially adjacent one another. In another example, the inner steerable catheter 116 may be radially within the steerable guide catheter 114 and both may be radially within the delivery sheath 112. In yet other embodiments, the delivery sheath 112 may have the steerable guide catheter 114, the inner steerable catheter 116, and a compression coil 118 radially within the delivery sheath 112, as shown in FIG. 2.

The coil 118 may be flexible during navigation and advancement of the elongated member 102 through the patient's vasculature. The coil 118 may be made of or include a wire that stacks when compressed to provide a longitudinal support to the elongated member 102. In some embodiments, a longitudinal compressive force may be applied to the coil 118 by a tension catheter 120 located in the elongated member 102. In other embodiments, a longitudinal compressive force may be applied to the coil 118 from a proximal end of the coil 118. For example, a handle may be positioned at a proximal end of the coil 118 and configured to apply a longitudinal force that may compress the coil 118 from the proximal end in the distal direction to stack the coil and provide structural support to the elongated member 102.

In some embodiments, the tension catheter 120 may be radially within and longitudinally overlapping the coil 118. In other embodiments, the coil 118 may be radially within the tension catheter 120. In yet other embodiments, a longitudinal compressive force may be applied to the coil 118 by one or more other elements of the elongated member 102. While the tension catheter 120 is described herein as having one or more tension elements positioned therein to provide longitudinal force, it should be understood that the tension catheter 120 may be any appropriate delivery catheter configured to provide a longitudinal force to one or more components of the elongated member 102.

In some embodiments, the delivery sheath 112 and the steerable guide catheter 114 may be coaxial with one another. For example, the delivery sheath 112 and steerable guide catheter 114 may share a longitudinal axis 124 therethrough. In other embodiments, the delivery sheath 112, steerable guide catheter 114, inner steerable catheter 116, coil 118, tension catheter 120, or combinations thereof may be coaxial and/or share the longitudinal axis 124 of the elongated member 102.

In some embodiments, at least one of the delivery sheath 112, steerable guide catheter 114, inner steerable catheter 116, coil 118, or tension catheter 120 may be a steerable element. For example, at least one of the delivery sheath 112, steerable guide catheter 114, inner steerable catheter 116, coil 118, and tension catheter 120 may have a plurality of tensioning elements, cables, threads, sutures, or chambers that may allow a lateral force to be applied to the element, as known in the art, to allow steerability of the elongated member 102.

In at least one embodiment, a friction-reducing layer and/or coating may be located between the delivery sheath 112 and the steerable guide catheter 114. In other embodiments, a friction-reducing layer and/or coating may be located on the delivery sheath 112 and/or steerable guide catheter 114 to reduce friction between the delivery sheath 112 and the steerable guide catheter 114. For example, a friction-reducing layer and/or coating may include a polytetrafluoroethylene (PTFE) layer positioned between or on the delivery sheath 112 and the steerable guide catheter 114. In other examples, other lubricious coatings, such as perfluoroalkoxy (PFA), fluorinated ethylene propylene, other fluoropolymers, ceramic coatings, one or more materials combined with a polymer structure (such as PROPELL available from FOSTER CO.), other materials, or combinations thereof, may be applied between the elements of the elongated member 102 to reduce friction between the elements during movement relative to one another. In yet other examples, a hydrophilic or hydrophobic layer may be positioned between and/or on the delivery sheath 112 and the steerable guide catheter 114.

Figure 3A:
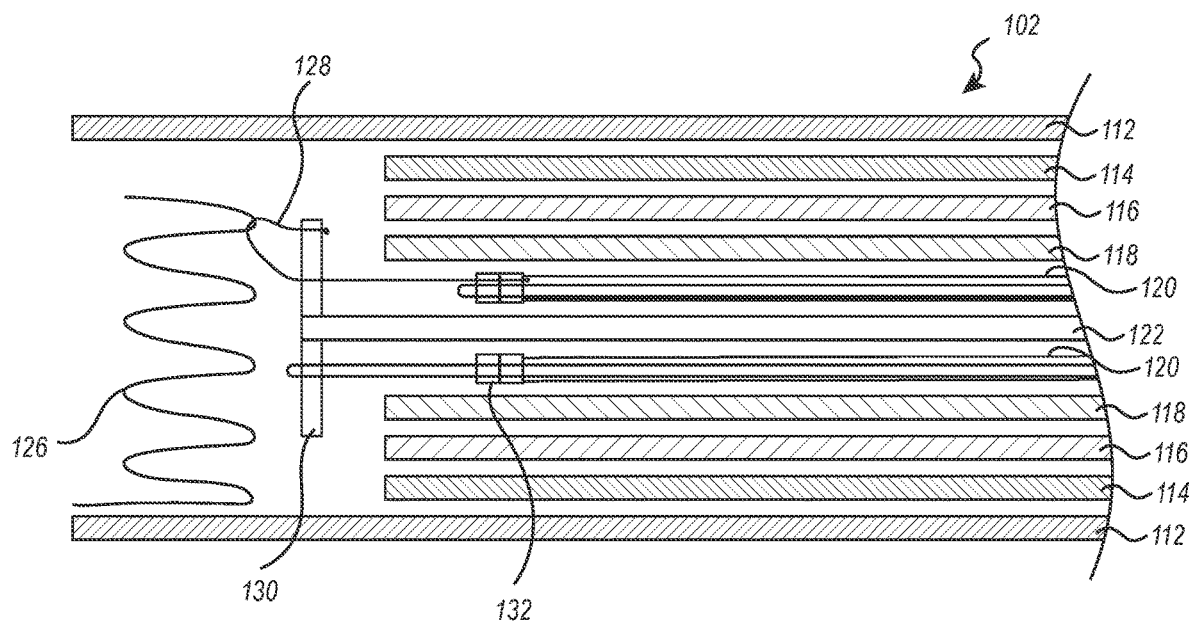
FIG. 3A is a side cross-sectional view of an embodiment of the distal end of the elongated member of FIG. 1, according to the present disclosure.
Figure 3B:
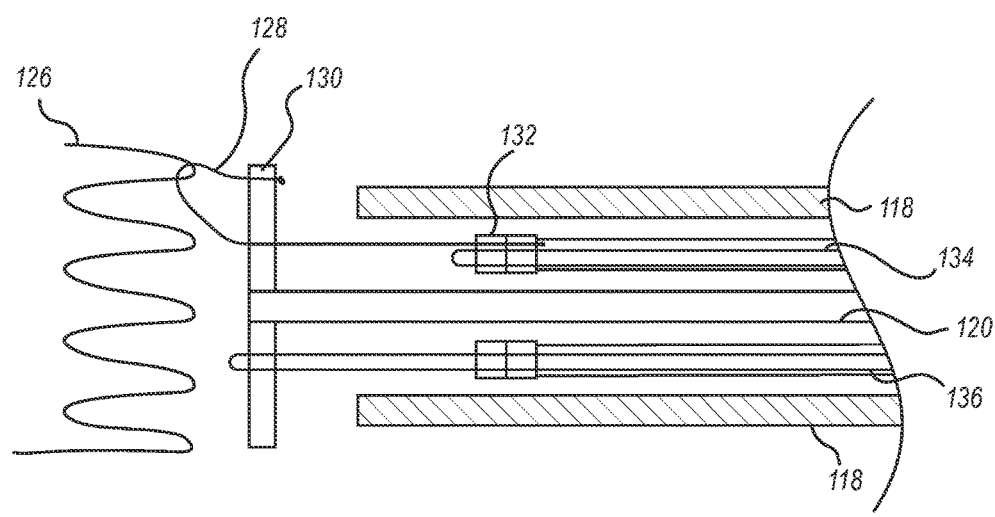
FIG. 3B is a detail view of the embodiment of the distal end of the elongated member of FIG. 1, according to the present disclosure.

FIGS. 3A and 3B are side cross-sectional views of an embodiment of the distal end 106 of the elongated member 102 described in relation to FIG. 2. In some embodiments, the distal end 106 may have an intravascular device, such as a valve replacement device 126 as shown in FIG. 3A, positioned therein and/or connected thereto. For example, the valve replacement device 126 may be longitudinally adjacent a distal end cap 130. In some embodiments, the distal end cap 130 may be longitudinally fixed to the steerable guide catheter 114 and/or the inner steerable catheter 116. In other embodiments, the distal end cap 130 may be longitudinally fixed relative to the coil 118 and/or tension catheter 120. In some embodiments, the valve replacement device 126 may be removably connected to the distal end cap 130. For example, the distal end cap 130 may have one or more retention features (e.g., threaded, pins, grooves, resilient clips, etc.) thereon and the valve replacement device 126 may have one or more complimentary retention features thereon, such that the valve replacement device 126 may selectively engage with the distal end cap 130. In other embodiments, the valve replacement device 126 may abut the distal end cap 130 without interlocking, adhering, or otherwise connecting to the distal end cap 130.

The distal end 106 may have a delivery sheath 112 at least partially longitudinally overlapping the valve replacement device 126. In some embodiments, an intravascular device may be moveable between a contracted state and an expanded state. For example, a MITRACLIP valve repair device may have one or more moveable members that may be deployed radially away from a body of the device and beyond a width of the delivery sheath 112.

In other embodiments, the valve replacement device 126 may be a self-expanding valve replacement device 126 with a contracted state and an expanded state. For example, the valve replacement device 126 may be biased toward the expanded state such that the delivery sheath 112 holds the valve replacement device 126 in the contracted state, and a removal of the delivery sheath 112 (e.g., moving the delivery sheath 112 in a proximal direction) from a longitudinally overlapping position, such as shown in FIG. 3A, may allow the expansion of the valve replacement device 126 toward an expanded state. In some embodiments, the valve replacement device 126 may include a shape memory material ("SMM") such as a shape memory polymer and/or a shape-memory metal. For example, the valve replacement device 126 may include or be made of a nickel titanium alloy.

The valve replacement device 126 in a contracted state may apply an expansive force to the delivery sheath 112. The force experienced between the valve replacement device 126 and the delivery sheath 112 may create and/or increase a frictional force of the delivery sheath 112 and the valve replacement device 126 and/or the steerable guide catheter 114. In some embodiments, the frictional force while moving the delivery sheath 112 relative to the valve replacement device 126 and/or the steerable guide catheter 114 may be greater than 2 pounds (8.9 Newton), greater than 10 pounds (44.5 Newtons), greater than 20 pounds (89.0 Newtons), greater than 30 pounds (133.4 Newtons), greater than 40 pounds (177.9 Newtons), or greater than 50 pounds (222.4 Newtons). A proximal force greater than the frictional force may be necessary to move the delivery sheath 112 in a proximal direction relative to the valve replacement device 126 and/or the steerable guide catheter 114.

The valve replacement device 126 may expand radially outward beyond the delivery sheath 112 after proximal of the delivery sheath 112 relative to the valve replacement device 126. The delivery sheath 112 may move in a proximal or distal direction relative to the steerable guide catheter 114, inner steerable catheter 116, distal end cap 130, or combinations thereof. The distal end cap 130 may limit and/or prevent the proximal movement of the valve replacement device 126 during proximal movement of the delivery sheath 112. In embodiments with one or more retention features on the distal end cap 130 and the valve replacement device 126, the longitudinal and/or rotational position of the valve replacement device 126 relative to the distal end cap 130 may be fixed.

In some embodiments, loading and retention of the valve replacement device 126 is aided by a tensioning element 128 connected to the distal end cap 130 and/or the tension catheter 120. For example, a suture loop is formed and the suture loop is connected to the tension catheter 120 to connect the tension catheter 120 to the valve replacement device 126.

Disconnecting the valve replacement device 126 may include severing, cutting, breaking, removing, melting, unhooking or otherwise disconnecting the tensioning element 128 from the valve replacement device 126. In some embodiments, the tensioning element 128 may include or be made of tungsten, steel, titanium alloy, aluminum alloy, nickel alloy, other metals, a shape memory material (such as a shape memory alloy or shape memory polymer), inorganic polymer, organic polymer, glasses, ceramics, carbon materials, or other flexible material with sufficient tensile strength. In at least one embodiment, the tensioning element 128 includes or is made of a polymeric suture.

As shown in FIG. 3B, in some embodiments, the tensioning element 128 may be connected at or near a distal end of the tension catheter 120. In some embodiments, the tensioning element 128 may be connected to a pair of discs that are longitudinally displaceable relative to one another. In other embodiments, a suture loop may be connected to the tension catheter 120. In some embodiments, the distal end cap 130 is one of the two discs and the second disc is a delivery disc 132 longitudinally fixed relative to the tension catheter 120. In at least one embodiment, the delivery disc 132 includes a tensioning element release mechanism to disconnect the tensioning element 128 from the delivery disc 132. For example, the delivery disc 132 may include one or more electrically conductive elements configured to increase in temperature when an electrical current is applied thereto, the increased temperature may melt, burn, or otherwise sever the tensioning element 128 or a bond between the tensioning element 128 and the delivery disc 132. For example, the tension catheter 120 may be configured to provide electrical communication from a proximal end of the elongated member to the tensioning element release mechanism. In other examples, the delivery disc 132 may be configured to mechanically release the tensioning element 128. In yet other examples, the delivery disc 132 may be configured to mechanically cut or sever the tensioning element 128.

In yet another embodiment, the tension elements 128 are connected to the valve replacement device 126 in a way that the suture loop(s) are looped over connection member(s) (e.g., hooks, prongs, barbs, or other unidirectional connectors). When the tension on a suture loop is released, the tension catheter 120 can be pushed forward and the suture loop will slide off the connection member, thereby disconnecting from the intravascular device.

In other embodiments, the distal end cap 130 includes a tensioning element release mechanism to disconnect the tensioning element 128 from the distal end cap 130. For example, the distal end cap 130 may include one or more electrically conductive elements configured to increase in temperature when an electrical current is applied thereto, the increased temperature may melt, burn, or otherwise sever the tensioning element 128 or a bond between the tensioning element 128 and the distal end cap 130. For example, the coil 118 or other element of the elongated member may be configured to provide electrical communication from a proximal end of the elongated member to the tensioning element release mechanism. In other examples, the distal end cap 130 may be configured to mechanically release the tensioning element 128. In yet other examples, the distal end cap 130 may be configured to mechanically cut or sever the tensioning element 128.

In some embodiments, the delivery disc 132 may be longitudinally movable relative to the distal end cap 130 in a proximal direction (i.e., away from the distal end cap 130) by applying a tension force to a proximal cable 134 that extends through at least a portion of the tension catheter 120. The distal end cap 130 may be longitudinally movable relative to the delivery disc 132 in a distal direction (i.e., toward the distal end cap 130) by applying a tension force to a distal cable 136 that extends through at least a portion of the tension catheter 120. The proximal cable 134 and the distal cable 136 may connect to a disc handle 138 shown in FIG. 4. In some embodiments, a plurality of tensioning elements 128 may be embedded in the tension catheter 120 and move as one to deploy and/or release the valve replacement device 126.

In other embodiments, one or more of the tensioning elements 128 may extend through the tension catheter 120 from the valve replacement device 126 or other intravascular device to a proximal end of the delivery catheter. For example, one or more of the tensioning elements 128 may extend through the tension catheter 120 from the valve replacement device 126 or other intravascular device to the disc handle 138 shown in FIG. 4.

In such embodiments, the relative length of lumen through the tension catheter 120 through which the one or more of the tensioning elements 128 extend may change from deflection of the elongated member during navigation through the patient's vasculature. For example, lumen on opposite sides of the tension catheter 120 will experience different extension and/or foreshortening during deflection of the tension catheter 120. Therefore, the lumen in the tension catheter 120 through which the tensioning elements 128 run may be as close to the guidewire lumen 122 and/or longitudinal axis 124 of the elongated member (such as described in relation to FIG. 2) as possible.

Figure 4:
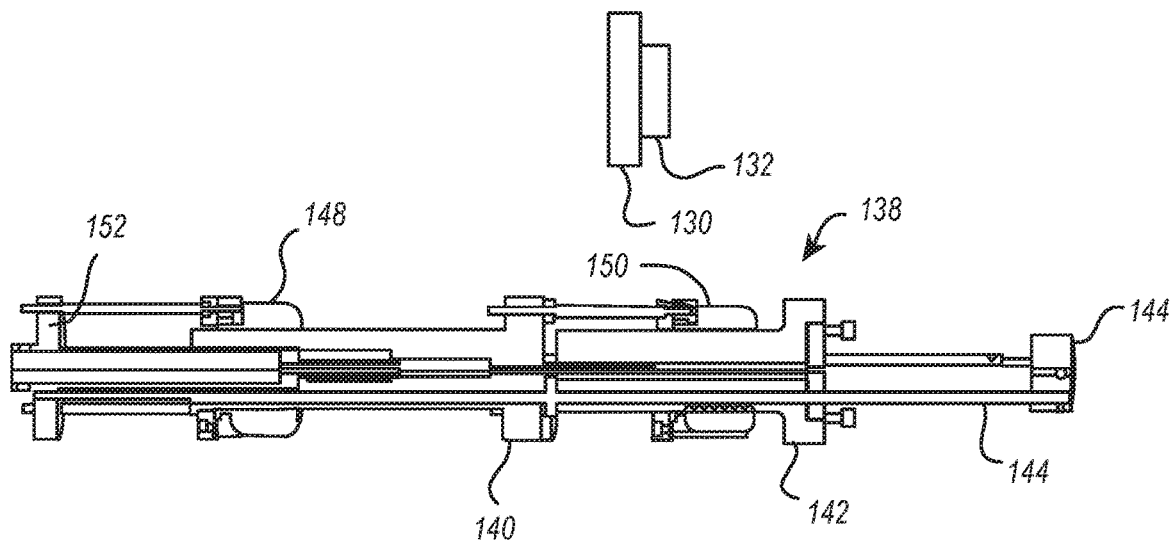
FIG. 4 illustrates an embodiment of a distal end cap and a delivery disc in relation to a side cross-sectional view of a disc handle, according to the present disclosure.

FIG. 4 through FIG. 9 illustrates a method of moving the distal end cap 130 and delivery disc 132 with a disc handle 138. FIG. 4 is a side cross-sectional view of a disc handle 138 with a main body 140, a movable body 142, and a rear body 144. In some embodiments, the main body 140 is movable in a longitudinal direction by rotation of a main body knob 148. In some embodiments, the movable body 142 is movable in a longitudinal direction (and relative to the main body 140) by rotation of a movable body knob 150.

The main body knob 148 may move the main body 140 in a longitudinal direction relative to a frame 152 of the disc handle 138. For example, the frame 152 may be connected to another control handle positioned in series with the disc handle 138 or connected to a stand configured to hold a series of control handles, where the various control handles control different elements of the elongated member and/or intravascular device. Connecting the frame 152 to the stand may hold the frame 152 stationary relative to the other elements of the intravascular device delivery system.

In some embodiments, the main body knob 148 is rotatable relative to the main body 140 and complimentarily threaded surfaces of the main body knob 148 and the main body 140 convert the rotational motion of the main body knob 148 to longitudinal motion of the main body 140. For example, the main body knob 148 is fixed relative to the frame 152 such that the main body 140 moves longitudinally relative to the frame 152.

In some embodiments, the movable body knob 150 is fixed longitudinally relative to the main body 140 and rotatable relative to the movable body 142. Rotation of the movable body knob 150 causes a threaded surface of the movable body knob 150 and a complimentarily threaded surface of the movable body 142 to engage and convert the rotational motion of the movable body knob 150 to longitudinal motion of the movable body 142 relative to the main body 140.

In at least one embodiment, the movable body 142 is longitudinally fixed to the main body 140 through the movable body knob 150 when the movable body knob 150 is stationary and/or fixed. For example, a first displacement between the main body 140 and the movable body 142 (and therefore an associated displacement between the distal end cap 130 and delivery disc 132) may be constant as the main body knob 148 is rotated and the main body 140 (and therefore the movable body 142 also) moves longitudinally relative to the frame 152. In another example, the movable body knob 150 may be rotated to move the movable body 142 longitudinally relative to the main body 140 and to a second displacement. Subsequent rotation of the main body knob 148 will move the main body 140 and movable body 142 longitudinally while maintaining the second displacement.

The movable body 142 is movable within the disc handle 138 relative to the main body 140 and the rear body 144 is longitudinally fixed relative to the main body 140. For example, the rear body 144 may be longitudinally fixed relative to the main body 140 by at least one rod 146. In at least one embodiment, the movable body 142 may be selectively fixed relative to the main body 140. For example, the movable body 142 may be fixed relative to the rod 146 such that the disc handle 138 is movable as a single body.

The main body 140 may be connected to the distal end cap 130 and the movable body 142 may be connected to the delivery disc 132. For example, the main body 140 may be connected to the distal end cap 130 by the coil (such as described in relation to FIG. 3B) and the movable body 142 may be connected to the delivery disc 132 by the proximal cable 134 and/or delivery catheter (such as described in relation to FIG. 3B). For example, proximal movement of the main body 140 may move the distal end cap 130 proximally, and proximal movement of the movable body 142 may move the delivery disc 132 proximally. In another example, distal movement of the main body 140 may move the distal end cap 130 distally, and distal movement of the movable body 142 may move the delivery disc 132 distally.

Before loading an intravascular device, the distal end cap 130 and delivery disc 132 are positioned near and/or adjacent one another. In some embodiments, the main body 140 and movable body 142 may be positioned near and/or adjacent one another when the distal end cap 130 and delivery disc 132 are positioned near and/or adjacent one another.

Figure 5:
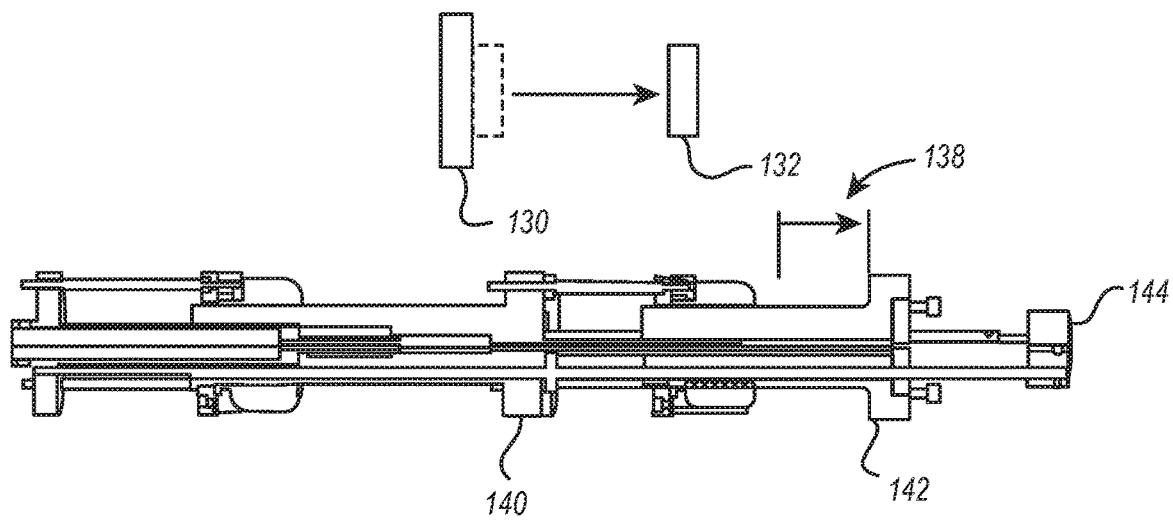
FIG. 5 illustrates the embodiment of a distal end cap and a delivery disc in relation to a side cross-sectional view of a disc handle while loading an intravascular device, according to the present disclosure.

As shown in FIG. 5, during loading of the intravascular device, the intravascular device may be connected to one or more tensioning elements (such as tensioning elements 128 described in relation to FIGS. 3A and 3B) and the intravascular device may be drawn proximally and/or radially contracted toward a contracted state by the tensioning elements by moving the delivery disc 132 in a proximal direction relative to the distal end cap 130. The delivery disc 132 may be moved in a proximal direction relative to the distal end cap 130 by moving the movable body 142 in a proximal direction relative to the main body 140 of the disc handle 138.

Figure 6:
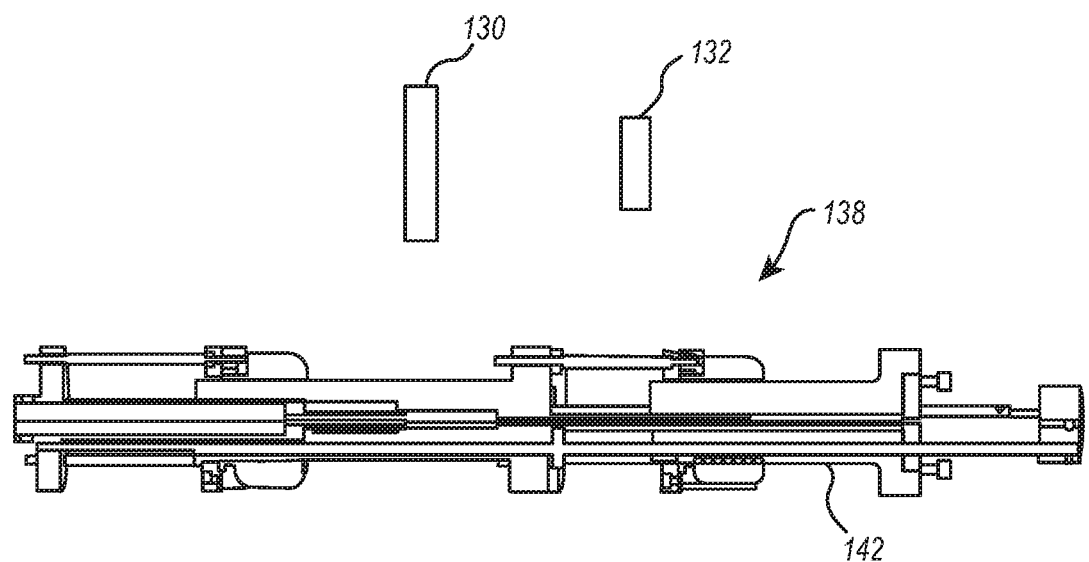
FIG. 6 illustrates the embodiment of a distal end cap and a delivery disc in relation to a side cross-sectional view of a disc handle while steering the intravascular device delivery system, according to the present disclosure.

Referring to FIG. 6, the distal end cap 130 and delivery disc 132 may remain stationary relative to one another during steering of the intravascular device delivery system through the patient's vasculature and positioning of the intravascular device at or near a target location. For example, the disc handle 138 may remain substantially stationary during steering. In some embodiments, the delivery disc 132 is moved toward the distal end cap 130 to reduce the tension on one or more cables during steering. For example, during steering through tortuous anatomy, decreasing tension on one or more cables may increase flexibility of the elongated member.

In yet another embodiment, the movable handle 142 may be moved distally to reduce and/or release tension on one or more of the tensioning elements 128. It is possible to reduce and/or release tension on one or more of the tensioning elements 128, since the valve replacement device remains compressed by the delivery sheath. Reducing and/or releasing tension may have positive effect on the steerability of the catheter.

Figure 7:
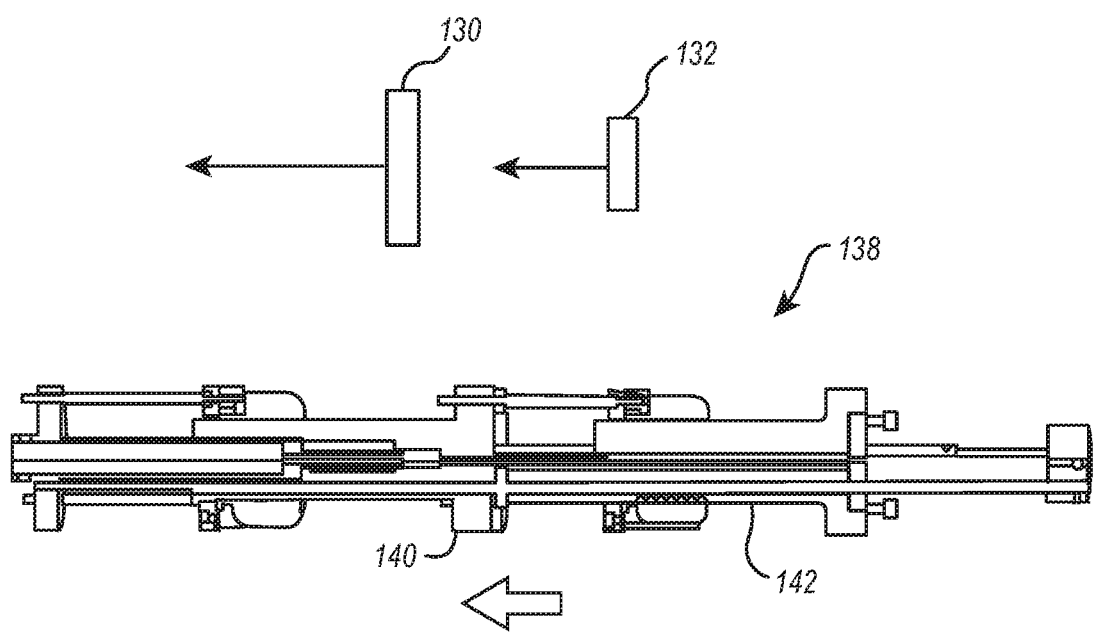
FIG. 7 illustrates the embodiment of a distal end cap and a delivery disc in relation to a side cross-sectional view of a disc handle during an embodiment of partial deployment of an intravascular device, according to the present disclosure.

Referring now to FIG. 7, the intravascular device may be deployed by urging the intravascular device out of the outer sleeve and allowing at least part of the intravascular device to expand radially. To urge the intravascular device out of the outer sleeve, the intravascular device may be urged distally by moving the distal end cap 130 and delivery disc 132 in a distal longitudinal direction. In some embodiments, the disc handle 138 is urged distally such that the main body 140 and the movable body 142 move together. For example, the main body 140 may be in communication with the coil described in relation to FIG. 3A and the coil may transmit compression force from the disc handle 138 through the distal end cap 130 to the intravascular device to push the intravascular device out of the outer sleeve.

Figure 8:
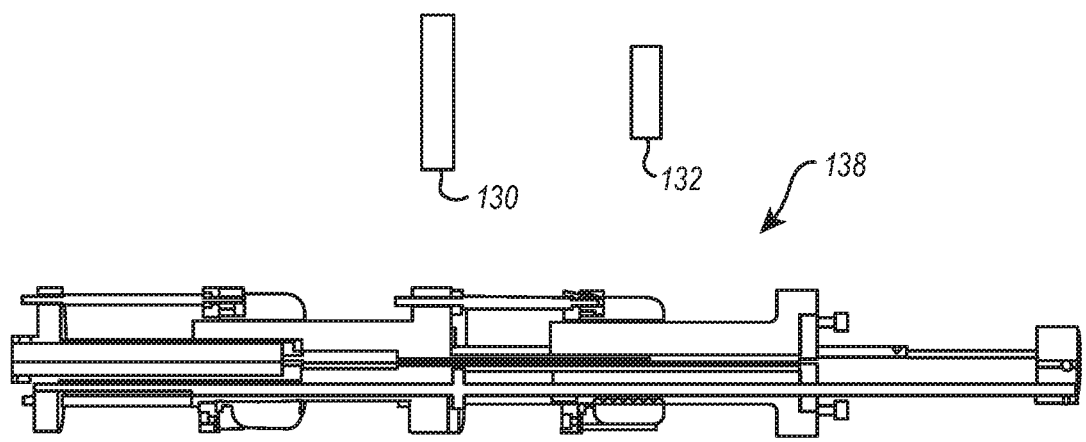
FIG. 8 illustrates the embodiment of a distal end cap and a delivery disc in relation to a side cross-sectional view of a disc handle during another embodiment of partial deployment of an intravascular device, according to the present disclosure.

In other embodiments, such as shown in FIG. 8, the intravascular device may be deployed by moving the outer sleeve in a proximal direction relative to the remainder of the elongated member. In such embodiments, the disc handle 138 may be substantially stationary during the movement of the outer sleeve. After distal movement of the distal end cap 130 and delivery disc 132 as shown in FIG. 7, or after proximal movement of the outer sleeve described in relation to FIG. 8, the intravascular device may be partially deployed. After partial deployment, the initial positioning of the intravascular device may be confirmed before completing deployment.

Figure 9:
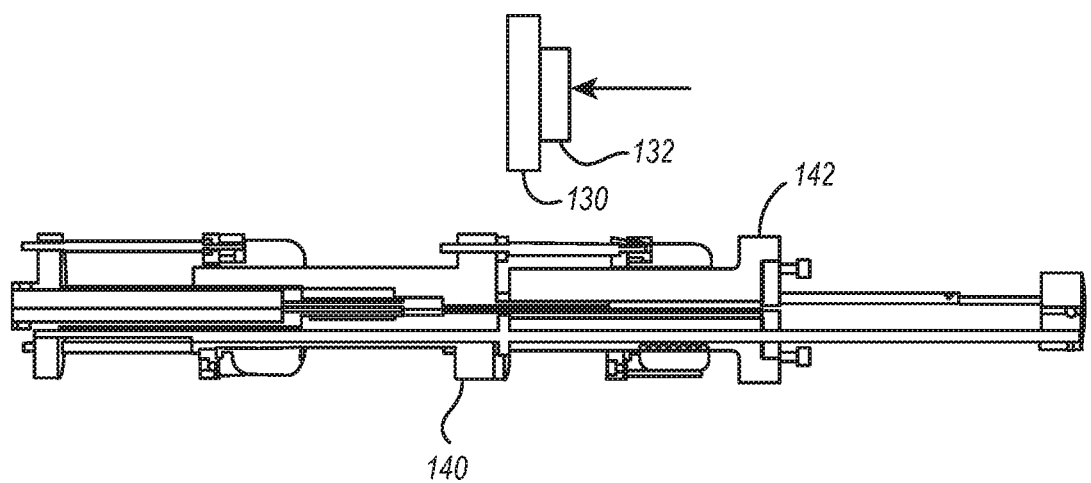
FIG. 9 illustrates the embodiment of a distal end cap and a delivery disc in relation to a side cross-sectional view of a disc handle during full deployment of an intravascular device, according to the present disclosure.

To complete deployment of the intravascular device, the delivery disc 132 is moved distally, for example toward and/or adjacent to the distal end cap 130, as shown in FIG. 9. The distal movement of the delivery disc 132 may move the one or more tensioning elements connecting the delivery disc 132 to the intravascular device distally, allowing the intravascular device to fully deploy from the intravascular device delivery system.

In some embodiments, after fully deploying the intravascular device from the intravascular device delivery system, the one or more tensioning elements are disconnected from the intravascular device, the delivery disc 132, and/or the distal end cap 130. As described herein, the delivery disc 132 and/or the distal end cap 130 may include a mechanism to disconnect the tensioning element 128 from the delivery disc 132 and/or the distal end cap 130. For example, the delivery disc 132 may include one or more electrically conductive elements configured to increase in temperature when an electrical current is applied thereto, the increased temperature may melt, burn, or otherwise sever the tensioning element 128 or a bond between the tensioning element 128 and the delivery disc 132. In other examples, the delivery disc 132 may be configured to mechanically release the tensioning element 128. In yet other examples, the delivery disc 132 may be configured to mechanically cut or sever the tensioning element 128.

In other embodiments, the suture loops 128 are hooked over a straight short hook located in the valve replacement device. In yet other embodiments, several suture loops might be connected to the valve replacement device. After releasing the tension of the suture loops, and after at least partially releasing and anchoring the valve replacement device, the tension catheter 120 and the compression coil 118 may be moved distally to slide the suture loop off the straight hook of the valve replacement device.

During navigation of the patient's anatomy, the elongated member of an intravascular device delivery system experiences a series of bends and rotations. The deflection of the elongated member may induce longitudinal displacement of at least a portion of one or more elements of the elongated member relative to one another. For example, a 90° turn in the elongated member will lengthen and/or foreshorten one or more of the elements relative to one another based, at least partially, on the diameter of the element, the constituent material(s) of the element, the thickness of the element walls, the construction of the element, or combinations thereof. In at least one example, a 90° turn in the elongated member may result in a greater foreshortening of the outer sleeve relative to delivery catheter and/or coil. The relative shortening of the outer sleeve may risk the premature deployment or partial deployment of the intravascular device.

Figure 10:
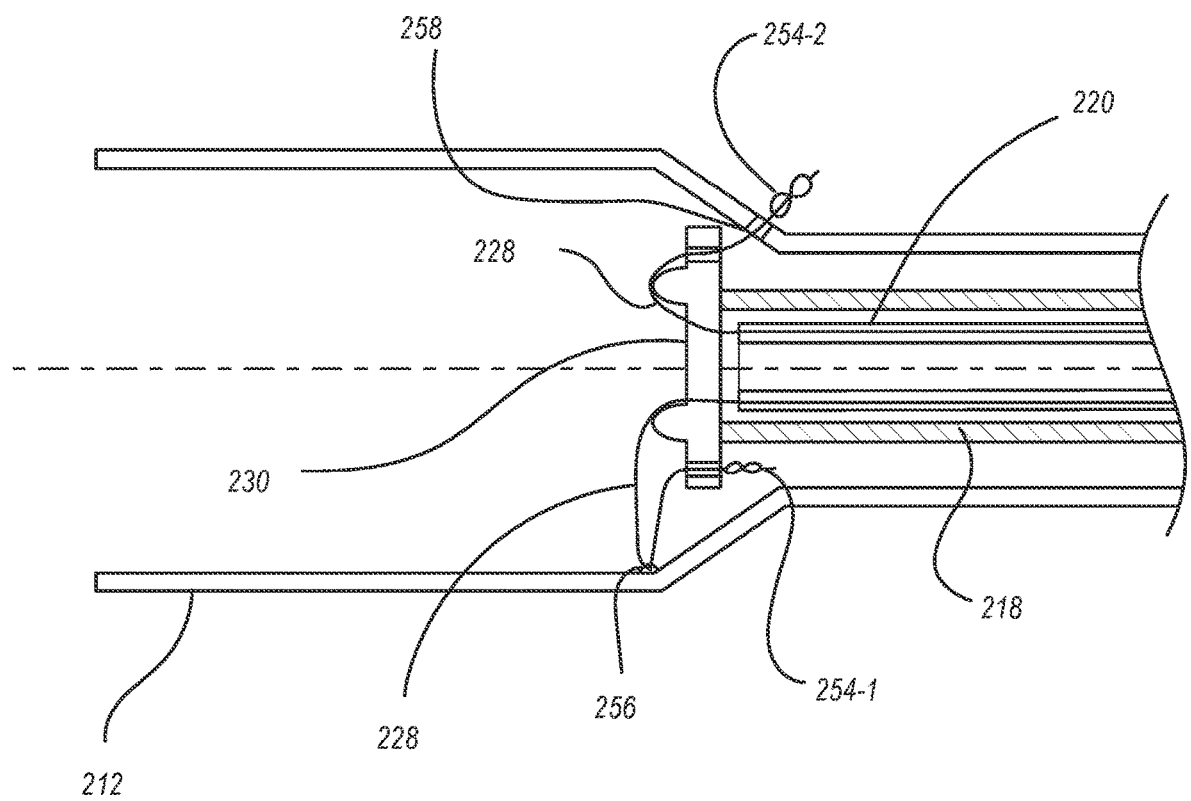
FIG. 10 illustrates a side cross-sectional view of an embodiment of a distal end cap and outer sleeve longitudinally fixed relative to one another, according to the present disclosure.

Referring now to FIG. 10, in some embodiments, the distal end cap 230 of the coil 218 and/or delivery catheter 220 is longitudinally fixed relative to the outer sleeve 212 at the distal end of the elongated member to limit the displacement of the outer sleeve 212 relative to the distal end cap 230 and, therefore, the intravascular device during navigation of the patient's anatomy. Note one or more elements of the elongated member may be omitted for clarity of description.

The main stress the outer sleeve 212 will experience during valve delivery will be tension stress. When the intravascular device is deployed from the outer sleeve 212, the outer sleeve 212 is fixed longitudinally relative to one or more elements of the elongated member and the compression coil 218 is advanced. Likewise, if the intravascular device is deployed by pulling the outer sleeve 212 proximally, the coil 218 will be kept stationary. During both procedures the outer sleeve 212 will be under tension stress. During delivery and during steering, the outer sleeve 212 has to have the ability to confirm to the different deflection planes.

Similarly, the coil 218 may be at least partially unstaged (i.e., the loops of the coil are not stacked or contacting one another) during steering of the elongated member, but may be staged during deployment. While the coil 218 is unstaged, the coil may displace longitudinally relative to the outer sleeve 212.

One or more embodiments may couple the outer sleeve 212 with the distal end cap 230. At least one tensioning element 228 is guided through one of the lumen of the inner delivery catheter 220. At the inside of the proximal end of the distal valve cover portion of the outer sleeve 212, at least one small eyelet 256 will be welded to said outer sleeve 212. The tensioning element 228 will exit at the distal end of the inner delivery catheter 220 through the distal end cap 230. The tensioning element 228 may loop through the eyelet 256 back through the distal end cap 230 and secured with a knot 254-1 or other anchoring mechanism such that the knot 254-1 or other anchoring mechanism cannot pass through the opening in the distal end cap 230.

In another embodiment, also shown in FIG. 10, the tensioning element 228 is positioned from the inner delivery catheter 220, through an opening in the distal end cap 130 and through an aperture 258 in the outer sleeve 212. The tensioning element 228 may be secured with a knot 254-2 or other anchoring mechanism such that the knot 254-2 or other anchoring mechanism cannot pass through the aperture 258.

In some embodiments, a displacement of the distal end cap 230 and the outer sleeve 212 is enabled by introducing slack to the tensioning elements 228 by allowing the tensioning elements 228 to move through the inner delivery catheter 220. In other embodiments, a displacement of the distal end cap 230 is enabled by severing, melting, breaking, or otherwise disconnecting the tensioning elements 228 from the outer sleeve 212 and/or distal end cap 230 by one or more of the methods and mechanisms described herein.

Figure 11:
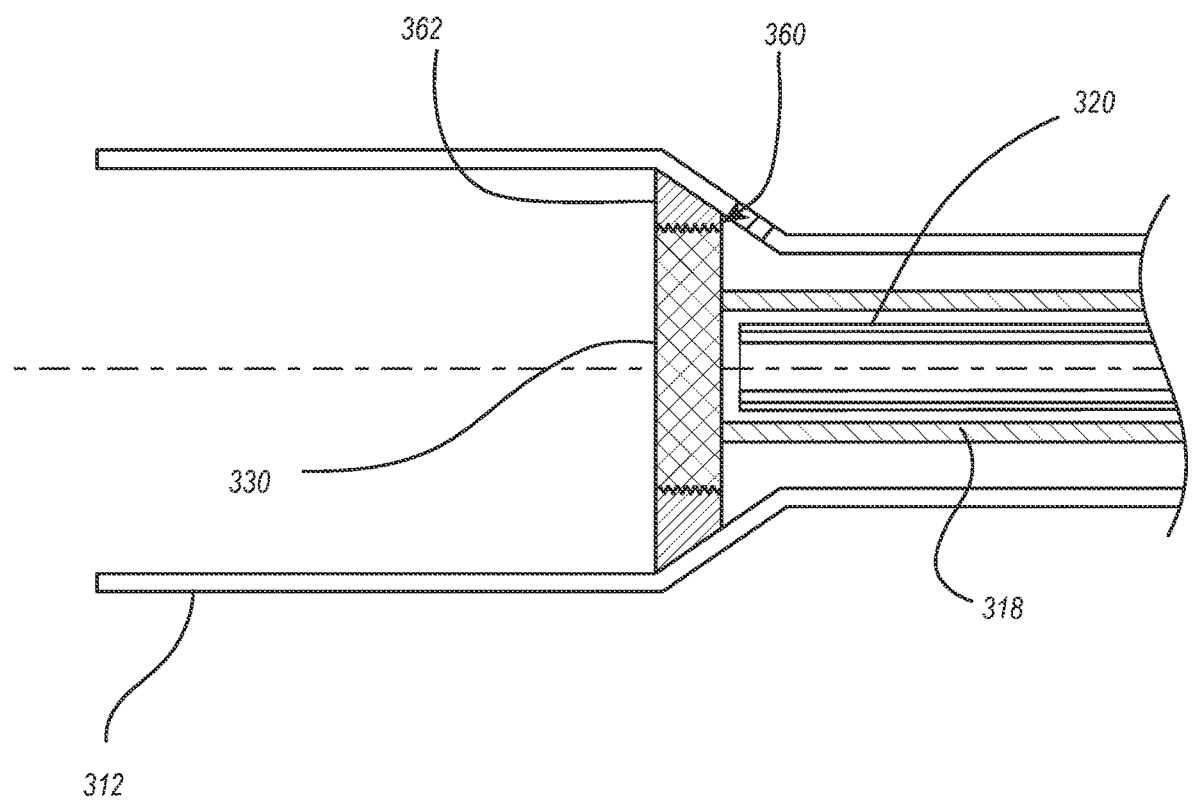
FIG. 11 illustrates a side cross-sectional view of another embodiment of a distal end cap and outer sleeve longitudinally fixed relative to one another, according to the present disclosure.

FIG. 11 illustrates another embodiment of an elongated member with a distal end cap 330 longitudinally fixed relative to an outer sleeve 312. FIG. 11 illustrates a mechanical interlock between the distal end cap 330 of the coil 318 and/or inner delivery catheter 320 and the outer sleeve 312. The distal end cap 330 may include a first mechanical interlocking feature, and the outer sleeve 312 may include a complimentary second mechanical interlocking feature.

For example, the first mechanical interlocking feature may be a first threaded surface 360 and the second mechanical interlocking feature may be complimentary second threaded surface 362. The first mechanical interlocking feature and second mechanical interlocking feature may interlock to limit and/or prevent the longitudinal movement of the distal end cap 330 relative to the outer sleeve 312.

In some embodiments, the first mechanical interlocking feature and second mechanical interlocking feature are a first threaded surface 360 on a radially outer surface of the distal end cap 330 and the second mechanical interlocking feature is a complimentary second threaded surface 362 on a radially inner surface of the outer sleeve 312. In other embodiments, the first mechanical interlocking feature and second mechanical interlocking feature includes a snap fit, a compression fit, a twist lock, a keyed lock, a pin, a hook, other mechanical features, or combinations thereof. In embodiments with a rotational interlock, the coil 318 may optionally including a cable tube configured to transmit torque from a proximal end to a distal end of the cable tube. The cable tube includes both a braid and a coil that provides flexibility and withstands tension forces during release of the intervascular device.

In some embodiments, the second mechanical interlocking feature is integrally formed with the outer sleeve 312. In other embodiments, the second mechanical interlocking feature is affixed to the outer sleeve 312, for example, by welding, brazing, an adhesive, a mechanical interlock, other fixation method, or combinations thereof.

Figure 12:
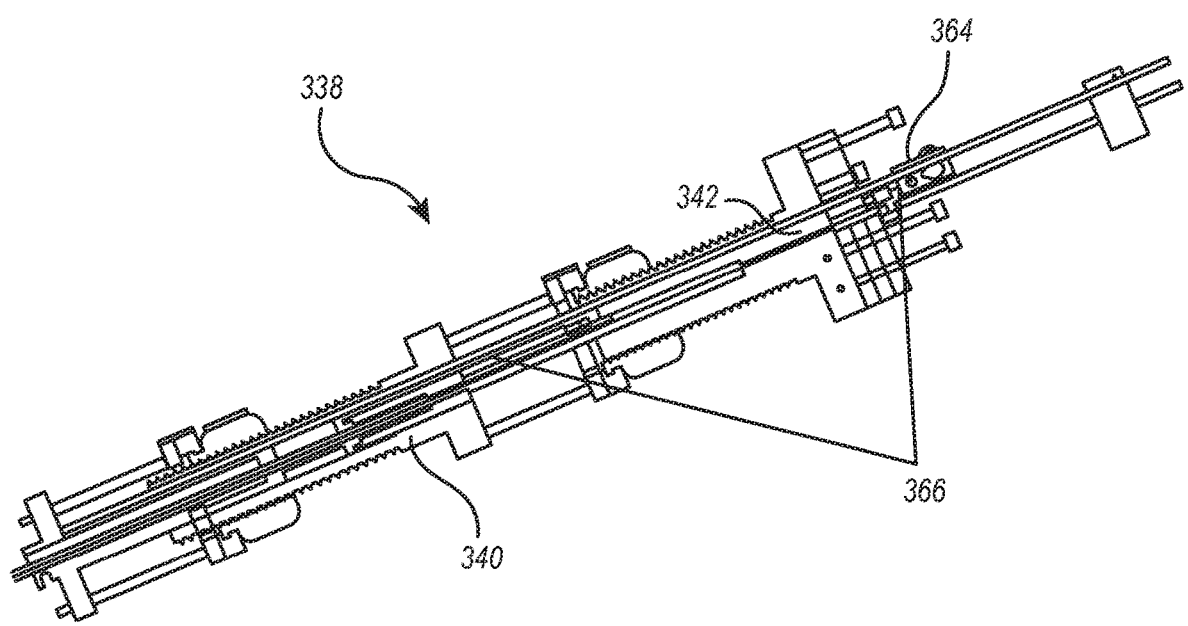
FIG. 12 illustrates a side cross-sectional view of a handle configured to operably couple to the embodiment of a distal end cap of FIG. 10, according to the present disclosure.

FIG. 12 illustrates an embodiment of a disc handle 338 with a main body 340 and a movable body 342 that is movable relative to the main body 342, similar to the disc handle 138 described in relation to FIG. 4 through FIG. 9. The disc handle 338 includes a tension device 364 (such as a spring, a clamp, or other mechanism described herein) to maintain a tension on the tensioning elements shown in FIG. 10.

To ensure the tension on the tensioning elements is approximately constant, the tension device 364 may be securable to a standoff 366 that extends through the main body 340 and movable body 342 to a handle distal of the disc handle 338, such as a steerable catheter handle. The tension device 364 is, therefore, selectively securable relative to the steerable catheter (or other element of the elongated member radially outside of the coil and delivery catheter. The disc handle 338 may then move the delivery disc relative to the distal end cap (as described in relation to FIG. 4 through FIG. 9 herein) without displacing the tension device 364 and altering tension on the tensioning element. Securing the tension device 364 relative to the standoff 366 connected to a handle distal of the disc handle 338 may, therefor, allow the distal end cap to be retained at or near the intravascular device during steering while allowing movement of the delivery disc.

In other embodiments, the tension device 364 may include a one way bearing or other ratcheting device. The one way bearing or other ratcheting device can be turned in one direction and increase tension on a tensioning element. This may maintain tension on the tensioning element and allow the distal endcap to remain connected with the outer sheath. After the intravascular device has been positioned accurately and the device is ready to be released, the tension of the suture may be reduced and/or released. Tension can be reduced and/or released by breaking or severing the tensioned element at the distal end, or by unclamping the one way bearing or other ratcheting device.

Figure 13:
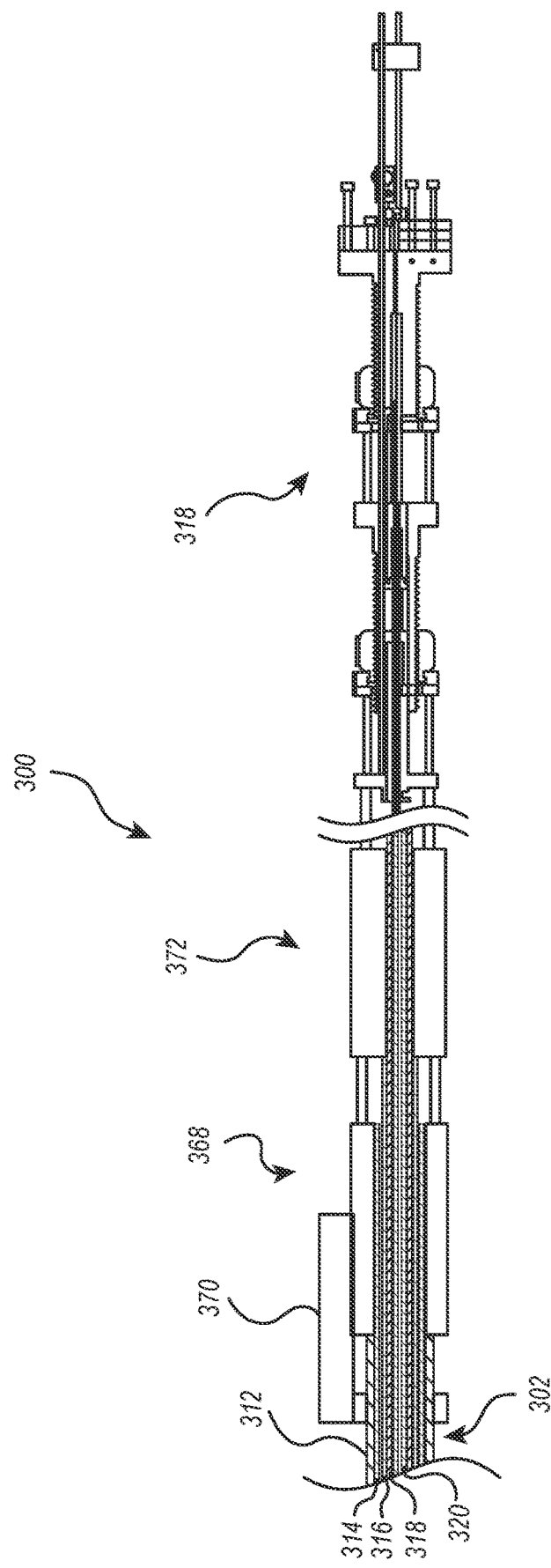
FIG. 13 illustrates a schematic side view of an embodiment of a series of handles configured to control an intravascular device delivery system, according to the present disclosure.

To further allow portions of elements of the elongated member to move relative to one another during steering, one or more elements may be decoupled relative to other elements at the proximal end of the element. For example, FIG. 13 illustrates an embodiment of an intravascular device delivery system 300 with a plurality of handles in series to control one or more element of the elongated member 302.

During steering the proximal end of the valve cover portion of the outer sleeve 312 may be longitudinally fixed relative to the distal end cap of the compression coil 318 and/or delivery catheter 320. During steering, the longitudinal length of the outer sleeve 312 relative to the longitudinal length of the compression coil 318 and/or delivery catheter 320 may change. The displacement between the outer sleeve 312 and the compression coil 318 and/or delivery catheter 320 may be accounted for by allowing the proximal part of the outer sleeve 312 to move longitudinally relative to the compression coil 318 and/or delivery catheter 320, while the distal portion of the outer sleeve 312 remains longitudinally fixed relative to the compression coil 318 and/or delivery catheter 320.

To allow the proximal part of the outer sleeve 312 to move longitudinally relative to the compression coil 318 and/or delivery catheter 320 (and the remainder of the elongated member 302, the outer sleeve 312 may be free-floating relative to remainder of the elongated member 302 during steering. For example, the outer sleeve 312 may be positioned radially outside of the steerable guide catheter 314, the deflection and axial movement of which is controlled by a steerable guide catheter handle 368. In some embodiments, the steerable guide catheter handle 368 includes an outer sleeve fixation device 370, such as a clamp, a pin lock, or other fixation mechanism, that allows for selectively securing the outer sleeve 312 relative to the steerable guide catheter handle 368 and, hence, the steerable guide catheter 312.

In some embodiments, the outer sleeve fixation device 370 may include a longitudinal displacement control relative to the steerable guide catheter handle 368. For example, the outer sleeve fixation device 370 may be secured to the outer sleeve 312, fixing the outer sleeve 312 longitudinally relative to at least the steerable guide catheter 314, and the longitudinal displacement control, such as an axial screw gear may displace the outer sleeve fixation device 370 relative to the steerable guide catheter handle 368.

The movement of the outer sleeve fixation device 370 in a longitudinal direction relative to the steerable guide catheter handle 368 moves the outer sleeve relative to steerable guide catheter 314 and/or other portions of the elongated member 302 to deploy the intravascular device. For example, the steerable guide catheter handle 368 may, in turn, be longitudinally securable relative to one or more other handles in the intravascular device delivery system 300, such an inner steerable catheter handle 372 located proximally of the steerable guide catheter handle 368 and/or the disc handle 338 described herein.

At least one embodiment of an intravascular device delivery system described herein may secure the distal portion of one or more elements of an elongated member relative to one another. The intravascular device may, therefore, be at a reduced risk of premature deployment as relative changes in longitudinal length of one or more element of the elongated member may occur in displacements of a proximal portion of the elongated member. After positioning the distal end of the elongated member bearing the intravascular device at a target location, one or more elements of the elongated member may be longitudinally fixed relative to one another to facilitate deployment of the intravascular device.

Flexible Cover

Figure 14:
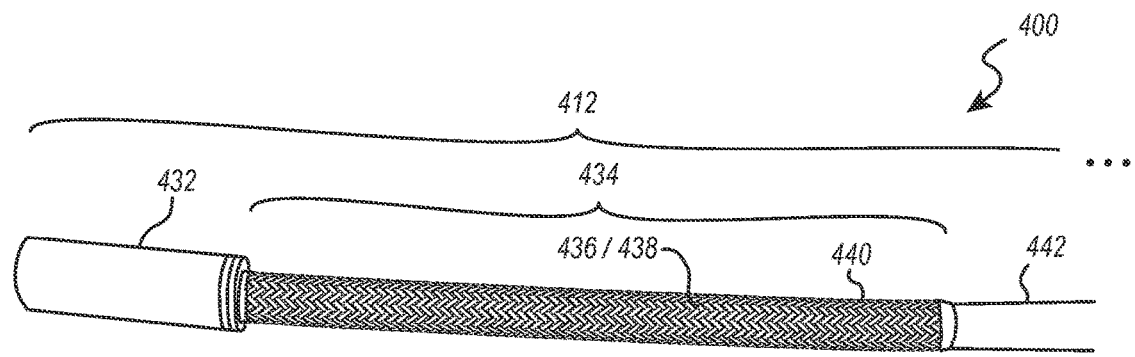
FIG. 14 illustrates a portion of the distal end of another embodiment of a delivery sheath.
Figure 15:
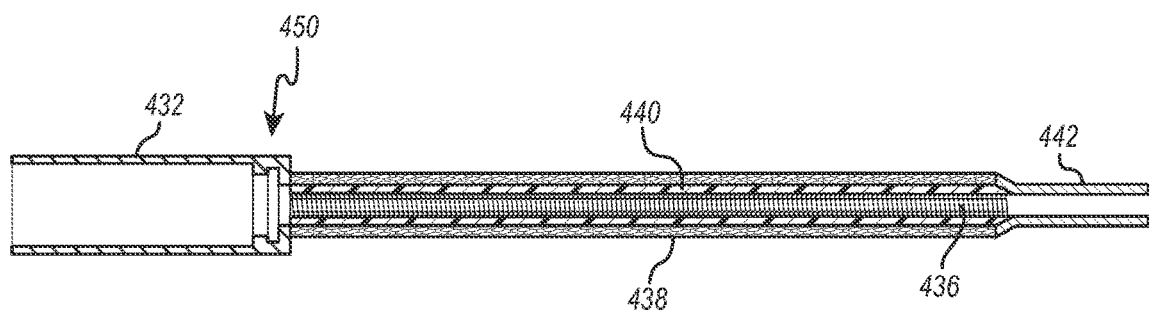
FIG. 15 is a cross-sectional view of FIG. 14.

In another embodiment, the delivery sheath can include an intravascular device cover ("ID cover") at its distal end and a flexible portion proximate and adjacent to the ID cover. FIGS. 14 and 15 illustrate a portion of the distal end of such an embodiment of delivery sheath 412, which includes a ID cover 432. ID cover 432 can be made of a steel cylindrical tube having an inner diameter and length sized to receive an intravascular device, in a collapsed configuration, within the lumen of ID cover 432. ID cover 432 can include a plurality of laser cuts and a pair of continuous longitudinal spines located on opposite sides so that ID cover can bend and flex substantially in a single plane. Delivery sheath 412 can also include a bending portion 434 that can be attached to and located proximal to ID cover 432. Bending portion 434 can preferably have a sufficient length to surround and extend along that portion of the delivery system 400 that is designed bend and reorient, via a steerable guide catheter 414, to navigate through a patient's vasculature and/or heart to a target site for deploying the intravascular device. In some embodiments, the bending portion 434 can include a cable tube or coil 436 surrounded by a braided structure 438 (sometimes collectively referred to as the "coil/braid portion 436/438") as shown in FIG. 16.

Figure 16:
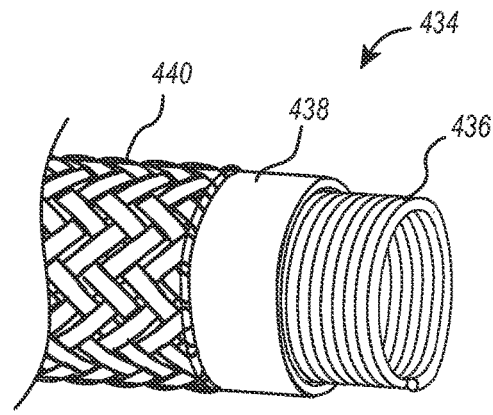
FIG. 16 is a partial cut-away view of an intermediate portion of the delivery sheath illustrated in FIGS. 14 and 15.

FIG. 16 is a perspective cutaway view of a hybrid delivery sheath 412. The delivery sheath 412 may have an inner cable tube or coil 436 and an outer braided sleeve or structure 438. Coil 436 can be made of or include a resilient coil material. For example, the coil material may be stainless steel, nickel titanium (e.g., Nitinol), other metal alloy, a thermoplastic, other polymers such as PEEK, ceramics, carbon tubing, glass, or combinations thereof. In at least one embodiment, coil 436 can be a stainless steel coil that has a droop value of 11:1 or higher. Coil 436 can be sized relative to the braided structure 438 such that the coil 436 has an outer diameter ("OD") in a relaxed state that is substantially the same as an inner diameter ("ID") of braided structure 438 in a relaxed state.

In some embodiments, braided sleeve 438 may include a plurality of threads or fibers that are woven together. For example, braided sleeve 438 may include a plurality of threads that extend at an angle to one another and are woven together in a repeating pattern. The plurality of threads may be woven in a diamond two wire two-under-two, over-two pattern; a half-load single wire over-one, one-under pattern; a full-load single wire over-two, under-two pattern; other alternating woven patterns; or combinations thereof. In other embodiments, braided sleeve 438 may include a single thread routed substantially straight longitudinally through the plurality of threads.

The threads may be round threads, elliptical threads, or flat threads. The threads may be made of or include a variety of reinforcement materials, such as, metals, metal alloys, thermoplastics, other polymers, ceramics, glasses or combinations thereof. In some embodiments, the reinforcement material or materials may have a greater elastic modulus than the body material. For example, a braided sleeve may include a mixture of threads with different properties, such as stainless steel threads woven with polymer threads. In at least one embodiment, braided sleeve 438 may include a plurality of 304 stainless steel wires woven in a diamond pattern. Such an embodiment of a braided sleeve may include between 16 and 72 threads of stainless steel. For example, braided sleeve 438 may include 24 strands, with each strand consisting of four wires.

In some embodiments, a hybrid delivery sheath, such as embodiments described in relation to FIG. 14 through FIG. 17, may transmit both compression and tension forces applied at a proximal end of the delivery sheath to the distal end of the delivery sheath without substantial change to the longitudinal length of the delivery sheath. In other embodiments, a hybrid delivery sheath may transmit tension force applied at a proximal end of the delivery sheath to the distal end of the delivery sheath without substantial change to the longitudinal length of the delivery sheath. For example, a hybrid delivery sheath may transmit tension force without substantial change to the longitudinal length of the delivery sheath and may foreshorten by 5%, 10%, 15%, 20%, 25%, 30%, 40%, 50%, 75%, 100%, 150%, 200%, 250%, 300%, 350%, 400% or any value therebetween during compression. In at least one embodiment, a coil may compress by a percentage of the initial longitudinal length of the delivery sheath before the coils contact one another and the coil transmits compression forces along the longitudinal length thereof. For example, the inner layer may be a coil with an initial spacing of between 0.1 mm and 5.0 mm, between 1 mm and 4 mm, between 2 mm to 3 mm, or any values therebetween to provide a bending radius to navigate the anatomy of a patient's heart.

Coil 436 and braided sleeve 438 may be longitudinally fixed to one another at or near a proximal end of the delivery sheath 412 and at or near the distal end of the delivery sheath 412. In some embodiments, the braided sleeve 438 may be welded or soldered to the coil 436 at a proximal end and at a distal end of the delivery sheath 412. In other embodiments, the braided sleeve 438 may be fixed to the coil 436 with an adhesive at a proximal end and a distal end of the delivery sheath 412. In yet other embodiments, the braided sleeve 438 may be fixed to the coil 436 via an intermediate element (e.g., an annular end cap) at a proximal end and a distal end of the delivery sheath 412. In yet other embodiments, braided sleeve 438 and coil 436 may be longitudinally fixed relative to one another at one or more points between a proximal end and a distal end of the delivery sheath 412. For example, braided sleeve 438 and the coil 436 may be longitudinally fixed relative to one another at a centerpoint.

Referring again to FIGS. 14 and 15, attached to the proximal end of bending portion 434 is a cut hypotube 442 that extends from bending portion 434 to the proximal end of delivery sheath 412 and a control fixture (not shown) used to manipulate the various component layers of the delivery system 400. Hypotube 442 can include a plurality of slits and at least one longitudinally continuous spine that can preferably be continuous and uninterrupted along a longitudinal length of, and located at a fixed angular location on, hypotube 442.

In some embodiments, the longitudinally continuous spine of hypotube 442 may allow the delivery sheath 412 to transmit tension force applied at a proximal end of the delivery sheath 412 to a distal end of the delivery sheath 412 without substantial elongation of the delivery sheath 412. In other embodiments, the longitudinally continuous spine hypotube 442 may allow the delivery sheath 412 to transmit compression force applied at a proximal end of the delivery sheath 412 to a distal end of the delivery sheath 412 without substantial shortening of the delivery sheath 412. For example, some embodiments of a delivery sheath 412, according to the present disclosure may exhibit a change in a longitudinal length of the delivery sheath 412 of 20% or less during application of both a compression force of 40 pounds (177.9 Newtons) or greater and a tension force of 40 pounds (177.9 Newtons) or greater. In other examples, some embodiments of a delivery sheath 412, according to the present disclosure may exhibit a change in a longitudinal length of the delivery sheath 412 of less than 5% during application of both a compression force of 40 pounds (177.9 Newtons) or greater and a tension force of 40 pounds (177.9 Newtons) or greater. In yet other examples, some embodiments of a delivery sheath 412, according to the present disclosure may exhibit a change in a longitudinal length of the delivery sheath 412 of less than 2% during application of both a compression force of 40 pounds (177.9 Newtons) or greater and a tension force of 40 pounds (177.9 Newtons) or greater.

In such embodiments, it can be desirable for the bending portion 434 of delivery catheter to remain liquid tight. To seal the bending portion 434, a flexible, fluid impermeable covering can be provided over the coil/braid portion 436/438, extending from the ID cover 432 to a location proximal the coil/braid portion 436/438. For example, the delivery sheath 412 can also include a thin walled flexible cover 440 that extends from the ID cover 432 to the hypotube 442. Flexible cover 440 can be bonded at each end to the underlying structure, using one of a variety of different adhesives, thermal adhesives, UV bonded adhesive, or other techniques. Flexible cover 440 can be fabricated from Pelathane 80A, Tecoflex 72A, Texin 70A, Chronoflex 45D, or other suitable flexible material. Flexible cover 440 can also be coated with hydrophilic coating. The wall thickness of flexible cover 440 could be between 0.001"-0.006" and preferably between 0.002"-0.004", and could have a diameter smaller than an outer diameter of the coil/braid portion 436/438.

Flexible cover 440 can be bonded at its distal end to a proximal end portion of ID cover 414 and can be bonded at is proximal end to a distal end portion of hypotube 442. An intermediate portion of flexible cover 440, including that portion that extends over the flexible coil/braid portion 436/438, is not bonded to flexible coil/braid portion 436/438, but rather can preferably be press fit or otherwise able to move relative to, and stretch over, flexible coil/braid portion 436/438. Flexible cover 440 can preferably be made of a material with some elasticity and can be attached at opposing ends to underlying structure in a way that it is stretched and normally retains some tension, which can help avoid wrinkles forming in flexible cover 440 when the delivery sheath 412 is bent or otherwise flexed. When flexible cover 440 is stretched onto the coil/braid portion 436/438 during fabrication, flexible cover 440 can foreshorten by up to 20%, but can easily stretch so as not to impair the flexibility of coil/braid portion 436/438.

Having the coil/braid portion 436/438 under a certain amount of pre-compression in some circumstances can also provide an advantage when recapturing the intravascular device. During deployment of the intravascular device, coil/braid portion 436/438 can be staged to supply the forces necessary to release the intravascular device from ID cover 432. Conversely, if recapture of the intravascular device should become necessary, coil/braid portion 436/438 can be stretched to the point where the braided structure 438 locks down on the coil 436 and can transmit high tension forces that may be needed to draw the intravascular device back into the ID cover 432. The stretching of flexible cover 440 also accommodates these relative movements of coil 436 and braided structure 438 within coil/braid portion 436/438. To facilitate fabrication, a mandrel can be disposed within the lumen of the delivery sheath 412, thereby stiffening delivery sheath 412, so that flexible cover 440 can be stretched and/or rolled over coil/braid portion 436/438, and then the opposing ends of flexible cover 440 can be sealed to the underlying structure.

Swivel Connection

Referring again to FIG. 15, delivery sheath 412 can also be coupled to ID cover 514 via a swivel connection, generally indicated at 450. To overcome the challenging forces that can develop during insertion of a large delivery catheter into the vasculature of a patient, swivel connection 450 allows rotation of delivery sheath 412 by a few degrees, back and forth (i.e., alternating between clockwise rotation and counter-clockwise rotation) while at the same time moving the delivery system 400 in a generally longitudinal direction. This rotational motion (during simultaneous longitudinal translation) helps to overcome some of the longitudinal forces that may resist insertion of delivery sheath 412 through a patient's vasculature.

However, in some embodiments the intravascular device can be positioned within and covered by the ID cover 432 and can also be connected to a delivery catheter positioned within the delivery system 400. Therefore, it might be desirable for an intermediate portion of the delivery sheath 412 (such as bending portion 434 and hypotube 442) to be free to swivel relative to the intravascular device and ID cover 432 while maintaining the intravascular device in stable and proper alignment with the delivery catheter of the delivery system 400. To facilitate this, the ID cover 432 can be rotationally decoupled from distal end of the delivery sheath 412 by providing a swivel connection between a proximal end portion of ID cover 432 and the distal end portion of delivery sheath 412. In the embodiment shown in FIG. 15, a first swivel connection 450 can be formed between the proximal end of ID cover 432 and the distal end of bending portion 434. For example, first swivel connection 450 can consist of an enlarged annular flange 452 welded to the distal end of the coil/braided sleeve 436/438, and flange 452 can be interposed between a pair of annular rings or ridges 454a and 454b formed on an inner surface of ID cover 432 at its proximal end. These structures cooperate to rotationally decouple the ID cover 432 from the bending portion 434, but at the same time maintain coupling between these elements in terms of longitudinal movement. While the illustrated embodiment uses cooperating flanges, rings and/or ridges, other suitable elements can also be used to accomplish the same functions, including, but not limited to rings, welds, detents, or other suitable structures. The first swivel connection 450 can also include one or more o-rings or other sealing components (not shown) positioned between the cooperating elements of the swivel to provide a fluid-tight swivel connection. A second embodiment of first swivel connection 450 is illustrated in FIG. 17.

Figure 17:
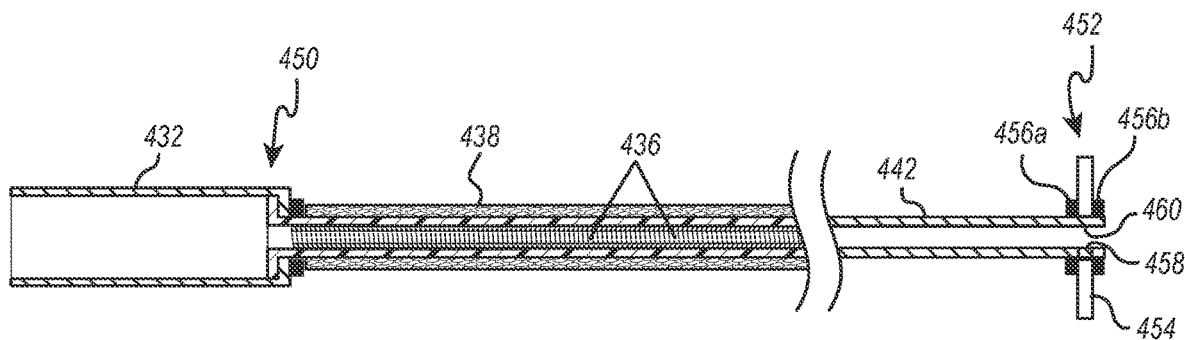
FIG. 17 is a cross-sectional view showing swivel connections between the valve cover and the delivery sheath and between the delivery sheath and the fixture.

Similarly, as further illustrated in FIG. 17, a second swivel connection 452 can also be formed at the proximal end of the delivery system 400 to rotationally decouple the delivery sheath 412 from the control fixture 454 (shown schematically only). Second swivel connection 452 can include a pair of spaced-apart, annular ridges 456a and 456b formed on the exterior surface and adjacent to the proximal end of hypotube 442. Annular ridges 456a and 456b form an annular recess 458 between which a complementary aperture 460 formed in fixture 454 can be positioned. Second swivel connection 452 can also include one or more o-rings or other sealing components (not shown) positioned between the cooperating elements of the swivel to provide a fluid-tight swivel connection.

Figure 18:
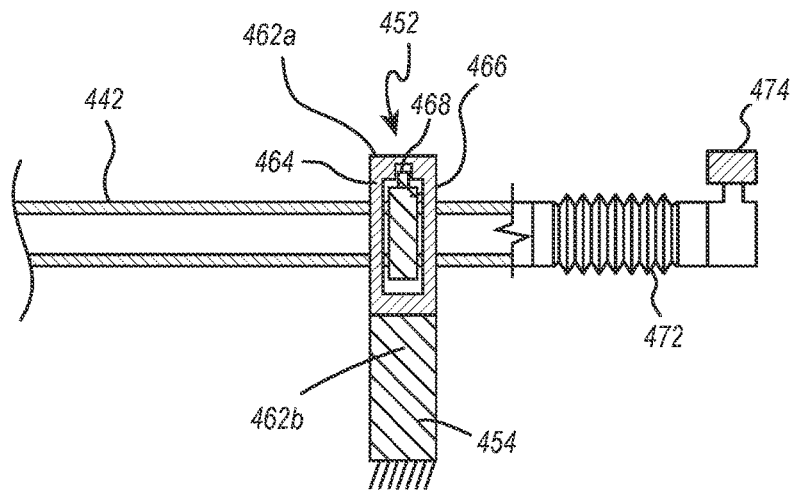
FIGS. 18 and 19 are cross-sectional views of an alternate embodiment of a swivel connection between the delivery sheath and the fixture.
Figure 19:
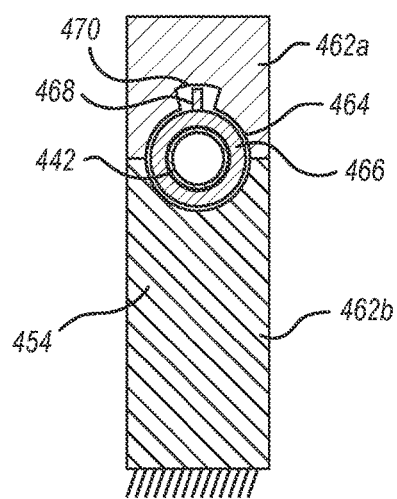

A second embodiment of second swivel connection 452 is illustrated in FIG. 18. In this embodiment, fixture 454 can provide a two-piece clamp 462a and 462b that includes an annular recess 464 that receives an annular ring 466 formed on the exterior of hypotube 442 at its proximal end. Ring 466 can easily be welded to the proximal end of hypotube 442. As further shown in FIG. 19, the ring can also have a pin 468 that extends into a complementary groove 470 formed in clamp 462. Pin 468 and groove 470 cooperate to limit rotation of ring 466 relative to clamp 462 within a predetermined swivel angle range (e.g., between plus and minus 15°), but any swivel angle can be accommodated by simply extending or reducing the length of groove 470.

As further illustrated in FIG. 18, an elastic bellow 472 can also be provided at the proximal end of hypotube 442. Bellow 472 allows a water tight connection, while at the same time accommodating rotational movement of hypotube 442. In addition, bellow 472 can stretch or compress when the delivery sheath 412 is moved longitudinally in a distal or proximal direction, as necessary, during delivery, deployment and/or release of the intravascular device. Finally, a standard luer lock connection 474 can be provided at the proximal end of bellow 472 to facilitate flushing of the interstitial spaces within delivery sheath 412 in preparation for an intervascular procedure.

Loading Assembly

Since tissue valves need to be stored in glutaraldehyde prior to use, unlike other intravascular devices like stents, coils, etc, a tissue valve to be delivered transvascularly cannot be pre-mounted to the delivery catheter. Therefore, the tissue valve has to be loaded into the delivery catheter in a cath-lab or medical facility. This can be difficult because the forces needed to open the tissue valve and maintain it in place make it difficult to collapse into a form sufficiently small to make it possible to transvascularly deliver the tissue valve.

To overcome the difficulties with loading tissue valves into a delivery device, the invention also provides loading assemblies and methods. As described above it is a challenge to load an intravascular device into a cover or sheath, if the intravascular device is to undergo a reduction in size and become compressed to a smaller diameter. Forces to load such an intravascular device, like a heart valve, can be 50 lbs or even higher.

In a case wherein the intravascular device is made from self-expandable material, such as a shape memory material, like Nitinol, the forces can be reduced by cooling the device. An efficient way to cool an intravascular device made from Nitinol is to submerge it into ice water (saline liquid) or a liquid below 32 degrees Fahrenheit. To ensure that the high loading forces do not have to be delivered through the length of the delivery catheter, a fixture can be provided to submerge and hold only the a distal end portion of the delivery system (e.g., the intravascular device and the valve cover).

Figure 20A:
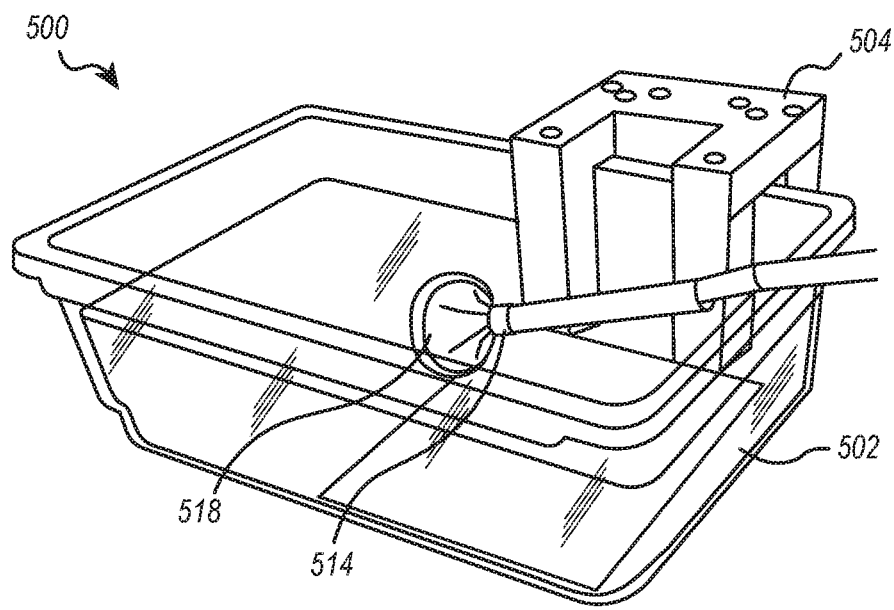
FIG. 20A is a perspective view of one embodiment of an assembly for loading an intravascular device into the distal end of a delivery system.
Figure 20A:
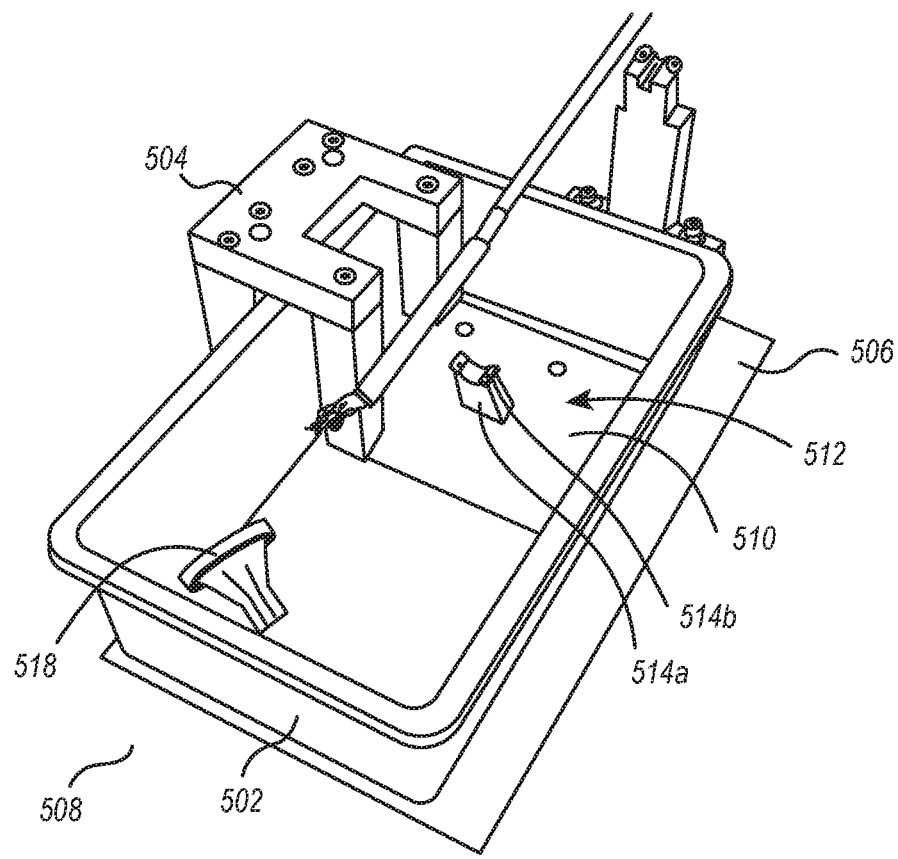
Figure 20B:
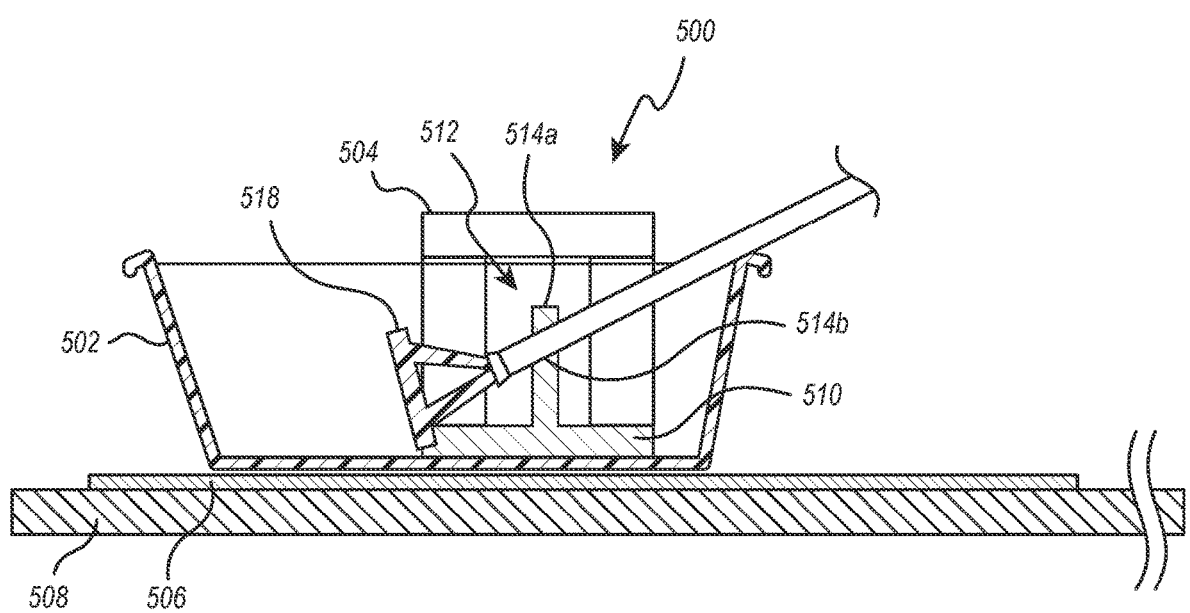
FIG. 20B is a cross-sectional view of FIG. 20A.

As illustrated in FIG. 20, loading assembly 500 can include a reservoir 502 for holding a ice/water bath (other liquid) that can lower the temperature of the tissue valve, and in particular the frame or Nitinol structure, to below its martensite transformation temperature. By loading the valve when its temperature is below the martensite transformation temperature, the loading process occurs in a low temperature phase in which any plastic or elastic deformation influenced by the valve during loading does not affect the final expanded deployed state of the tissue valve. In other words, once the temperature of the valve returns above the martensite transformation temperature, the valve will transition to the austenite phase and to the deployed, expanded configuration. In addition, the effect on the Nitinol also reduces the forces needed to pull in the tissue valve into the outer sheath or valve cover.

As further illustrated in FIG. 20, the loading assembly 500 can also include a fixture 504 that extends into an interior of the reservoir 502 on one side and mounts to a base member 506. Fixture 504 can transmit the forces to hold the valve cover to the base member 506 and then to a table or other support 508 that stabilizes the base member 506. Base member 506 and support 508 could be combined into a single support or structure for supporting reservoir 502 and one or more of the parts or portions of the loading assembly 500.

Fixture 504 can overlap a portion of reservoir 502 with a lower portion 510 submerged in the liquid. Lower portion 510 can be inclined to accommodate an angular orientation of outer sleeve or sheath or a portion of the elongate member. In another embodiment, lower portion 510 need not be inclined, but can be generally parallel to a bottom portion of the reservoir 502 or the base member 506.

Extending from lower portion 510 can be a clamping assembly 512 configured to receive and retain the outer sleeve, sheath, or valve cover relative to reservoir 502 and fixture 504. Clamping assembly 512 can include two half rings 514a and 514b that can be selectively connected by screws or other suitable fasteners. To simplify and speed up the procedure in a cath-lab, clamping assembly 512 can also include a quick engagement/release mechanism. For example, one side of each of the two half rings is pivotally mounted together and the other side includes a quick engagement/release lever and mechanism, such as an eccentric clamp or other toggle release. In another embodiment, a single half ring can be mounted to body 516 of the clamping assembly 512 that has formed therein a curved portion to receive the outer sleeve, sheath, or valve cover. In another embodiment, clamping assembly 512 can also be disposed outside of the reservoir 502, but mounted to the base member 506. In either embodiment, clamping assembly 512 securely supports and maintains the valve cover in a stationary position within the ice/water bath, while allowing axial movement of other component layers of the delivery system relative to the valve cover.

As further illustrated in FIG. 20, loading assembly 500 can also include a guiding member 518 that guides the tissue valve into the valve cover or outer sheath. Guiding member 518 can be disposed on the end of the valve cover or outer sheath prior to attaching the valve to the delivery system. In another embodiment, guiding member 518 could be formed in two pieces that can be selectively coupled together, which would allow it to be placed around a portion of the valve cover or outer sheath after the intravascular device is partially attached to the intravascular device delivery system, but before it is drawn into or towards the valve cover or outer sheath. In one embodiment, guiding member 518 can be a funnel-shaped C-cone.

Figure 21:
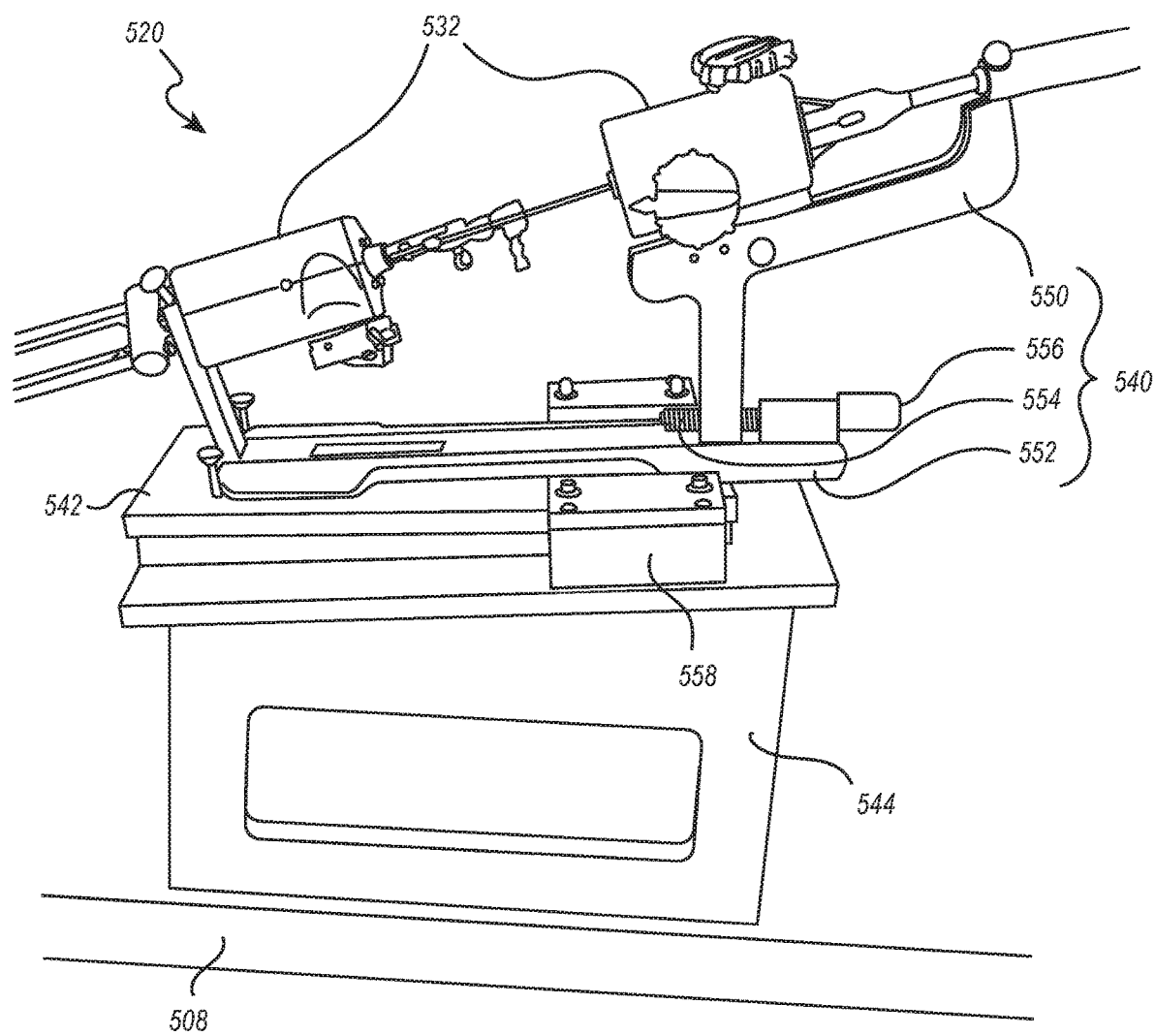
FIG. 21 is a perspective view of one embodiment of a control fixture located at the proximal end of the delivery system.

Referring next to FIG. 21, located at the other end of the intravascular device delivery system is a control fixture 520 that can be connected to the proximal end of, and can be used to control relative movement of, the various component layers of the delivery system. Control fixture 520 can include handle portions 532 are fixed to a stabilizer 540 positioned on a sliding support 542, with a locking mechanism 558 maintaining stabilizer 540 on sliding support 542. Sliding support 542 in turn is supported by a base member 544. Base member 544 (of control fixture 520) and base member 506 (of loading assembly 500) are fixed relative to each other so that, in the illustrated embodiment, base members 506 and 544 do not move relative to each other. Rather, sliding support 542 and other portions connected to sliding support 542 (such as an upper portion 550) can be selectively moved relative to a lower portion 552 through rotation of a threaded member or 554 by rotating a knob 556.

Sliding support 542 moves along rails 548 that can allow sliding support 542 to move relative to base member 544 both towards and away from base member 506. Movement of sliding support 542 can provide for macro adjustment of movement and/or positioning of the delivery system, and while movement of stabilizer 540 can provide micro or finer adjustment of movement and/or positioning of the delivery system, it will be understood that both or either can be used for macro and micro movement and/or positioning. In addition, sliding support 542 can move to varying degrees relative to the base member 544. For example, in one embodiment, the relative movement can be about 80 cm on either side of the base member 544, about 80 cm total travel from one side to the other side of the base member 544, about 0 cm to about 40 cm travel on both sides of base member 544, about 20 cm to about 40 cm travel on both sides of base member 544, or other distances of travel as may be necessary for a particular procedure. In addition, because the micro or fine adjustment/movement can occur through rotation of the threaded rod or member 554, high pull forces can be applied in a controlled manner to pull the tissue valve into the outer sheath or valve cover. This micro or fine adjustment/movement can also pull back the entire delivery system when needed.

In one configuration, during the process of pulling in the intravascular device into the cover, the sheath connected to the valve cover can be disconnected from the rest of the intravascular device delivery system so that the compression coil or cable tube forming part of the sheath or catheter can move, such as stretch for at least a distance to pull in the valve into the valve cover. This might be possible through using the flexible coil/braid construction or cable tube construction that can be compressed, depending on the design, by 20% or more. As an example if the collapsed valve is 35 mm long the length the sheath can stretch at least 35 mm. If the length of the flexible coil/braid element is 10 cm the compression can be at least 35%, in one configuration.

In one configuration, the method for loading the intravascular device, such as a valve, into a distal cover of the intravascular device delivery system can include one or more of the following actions, with it being understood that the number and order of these actions or steps can be varied. The method can include: removing the intravascular device, such as a valve, from a storage container that contains glutaraldehyde or other sterilizing or disinfectant solution; rinsing the intravascular device, such as a valve, in a solution, such as a saline solution; connecting the intravascular device, such as a valve, to the delivery catheter as described herein; clamping the valve cover into a loading assembly 500, via a clamping assembly 512; filling reservoir 502 with a liquid, such as ice and saline solution; verifying that a distal portion and a proximal portion of loading assembly 500 is secured for movement, such as verifying that base member 506 is secured to a table or other support 508 and that stabilizer 540 is secured to base member 544 or other table or support; and actuating stabilizer 540, such as by rotating knob 556 to pull back a reminder of the intravascular device delivery system, while maintaining the valve cover stationary to pull the intravascular device into the cover.

As set forth above, the invention includes various aspects. In one aspect, the invention can be directed to intravascular device delivery systems that can include: an elongated member having a distal end and a proximal end with a longitudinal axis extending therebetween, the elongated member including, a coil, a distal end cap longitudinally fixed to the coil, a delivery catheter positioned longitudinally overlapping at least a portion of the coil, and a delivery disc longitudinally fixed to the delivery catheter; and a disc handle configured to move the distal end cap and delivery disc, the disc handle including, a main body distal end cap configured to move the distal end cap, and/or a movable body configured to move the delivery disc longitudinally relative to the distal end cap. The intravascular device delivery systems can also: include a distal cable configured to transmit tension from the main body to the distal end cap; include a proximal cable configured to transmit tension from the movable body to the distal end cap; the movable body can also be configured to be selectively fixed relative to the main body; include at least one tensioning element connected to the distal end cap or the delivery disc; the at least one tensioning element can be a suture; the distal end cap or delivery disc can also include a tensioning element release mechanism; the tensioning element release mechanism can also include one or more electrically conductive elements; include intravascular device positioned adjacent the distal end cap; the distal end cap can be selectively longitudinally fixed to the outer sleeve; the intravascular device can be connected to the delivery disc with at least one tensioning element; the delivery catheter can also be configured to provide electrical communication to the tensioning element release mechanism; and/or the at least one tensioning element can connect the outer sleeve to the disc handle.

In another aspect, the invention can be directed to methods of deploying an intravascular device including: loading an intravascular device to a distal end of an intravascular device delivery system, positioning the intravascular device at a target location, partially deploying the intravascular device from the intravascular device delivery system, repositioning the intravascular device, and fully deploying the intravascular device from the intravascular device delivery system. The methods of deploying an intravascular device can also: include releasing at least one tensioning element connected to the intravascular device; releasing the at least one tensioning element can also include heating at least one electrically conductive element; the partially deploying the intravascular device can also include advancing a distal end cap longitudinally to urge the intravascular device longitudinally relative to an outer sleeve; and/or the intravascular device can be a self-expanding device.

In yet another aspect, the invention can also be directed to any device, apparatus, system, kit, component, or subcomponent as illustrated or described herein, or method of manufacture or use thereof.

In yet a further aspect, the invention can be directed to intravascular device delivery systems that can include: an elongated member having a distal end and a proximal end with a longitudinal axis extending therebetween, the elongated member including, an outer sleeve having a proximal end and a distal end, and a portion of the distal end being rotatably relative to a remainder of the outer sleeve. The intravascular device delivery systems can also: the rotating portion can rotate about a longitudinal axis of the outer sleeve; the rotating portion can have a length approximating a length of the intravascular device; the proximal end can be configured to rotate relative to the portion; include a sealing member extending from the portion towards the proximal end of the elongated member; the sealing member can seal a flexible region of the elongated member that extends from the portion to a location distal the proximal end of the elongated member; a first end of the sealing member can be mounted to the portion and a second end of the sealing member can be mounted to a location proximal a flexible region of the elongated member; an intermediate portion of the sealing member can be mounted to at least the portion and can be freely movable relative to the elongate member; include at least one steerable catheter positionable within at least a portion of the outer sleeve; include a coil positioned longitudinally overlapping and radially within at least a portion of the outer sleeve; include a distal end cap longitudinally fixed to the coil; include a delivery catheter positioned longitudinally overlapping and radially within at least a portion of the coil; include a delivery disc longitudinally fixed to the delivery catheter and positioned within the coil; include a disc handle configured to move the distal end cap and delivery disc; and/or the disc handle can include a main body configured to move the distal end cap longitudinally and a movable body configured to move the delivery disc longitudinally relative to the distal end cap.

In still another aspect, the invention can be directed to loading assemblies for aiding with loading an intravascular device into an intravascular device delivery system that can include: a fixture to support a proximal end of the intravascular device delivery system, another fixture to support a distal end of the intravascular device delivery system, and a reservoir to receive a portion of the intravascular device delivery system and an unloaded intravascular device. The loading assemblies can also: provide the another fixture comprises an angularly orientated support and a member extending into the reservoir; the another fixture can include a base member from which the member extends, and the member can be configured to transmit forces to the base member; include a support extending from an angularly orientated support of the another fixture; include another support extending form the base member; the fixture can include a base member and a sliding support selectively movable along at least a portion of the base member; include a locking mechanism to receive a stabilizer that supports the proximal end of the intravascular device delivery system; include a tip alignment assembly; the tip alignment assembly can include a lumen to receive a portion of an outer sheath of the intravascular device delivery system and a distal tip of the intravascular device delivery system, the lumen aiding to align the outer sheath and the distal tip; and/or the lumen can include an interior surface complementary to an outer surface of the distal tip and the outer sheath.

In still yet a further aspect, the invention can be directed to stabilizers for supporting an intravascular device delivery system that can include: a base and a plurality of mounts to receive a proximal end of the intravascular device delivery system, the plurality of mounts being selectively movable relative to the stabilizer base. The stabilizers can also: include a stabilizer base and a sliding member mountable to a sliding mechanism; the stabilizer base can be pivotally mounted to the sliding member; the base can include a stabilizer base with at least one mount of the plurality of mounts extends from the stabilizer base; include a micro adjustor to move at least one mount of the plurality of mounts relative to a base; include a macro adjustor to move at least one mount of the plurality of mounts relative to a base; include a combination micro and macro adjustor; include a secondary sliding member disposed at a proximal end of the stabilizer; and/or one of the plurality of mounts can be supported by the secondary sliding member.

The invention can be directed to methods for delivering an intravascular device, including: preparing an intravascular device for loading into an intravascular device delivery system, mounting a distal tip of the intravascular device delivery system to a guidewire tubular member, moving the intravascular device into a cover, mounting the distal tip to the cover, releasing a tension on a portion of the intravascular device delivery system, flushing the intravascular device delivery system, advancing the intravascular device delivery system towards a target location, advancing the intravascular device delivery system through a septum, position the intravascular device near a mitral annulus, advance the intravascular device through at least a portion of the mitral annulus, tension a tensioning element connecting the intravascular device to the intravascular device delivery system, unsheathing at least a portion of the intravascular device from the cover; and disconnecting the intravascular device from the intravascular device delivery system. Another method of delivering an intravascular device can include: preparing an intravascular device for loading into an intravascular device delivery system, moving the intravascular device into a cover, advancing the intravascular device delivery system towards a target location, unsheathing at least a portion of the intravascular device from the cover, and disconnecting the intravascular device from the intravascular device delivery system. The methods for delivering an intravascular device can also: include flushing portions of intravascular device delivery system; unsheathing at least the portion of the intravascular device delivery system can also include unsheathing an arterial disk of the intravascular device while maintaining a remainder of the intravascular device within the cover; include preventing the intravascular device to move distally during unsheathing of the at least the portion of the intravascular device; include moving one or more mounts of a plurality of mounts of a fixture supporting the intravascular device delivery system to selectively move one or more of the cover, the intravascular device, a distal tip, a guidewire tube, a delivery catheter, and a compression element; and/or include moving one or more mounts of a plurality of mounts of a fixture supporting the intravascular device delivery system to selectively move one or more of the cover, the intravascular device, a distal tip, a guidewire lumen, a tension member, and a compression member The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. An intravascular device delivery system for delivery of an intravascular device, the system comprising:
    an intravascular device, and
    an elongated member having a distal end and a proximal end with a longitudinal axis extending therebetween, the elongated member including:
        a coil extending from the proximal end of the elongated member toward the distal end of the elongated member,
        a distal end cap longitudinally fixed to a distal end of the coil and positioned within an intravascular device cover that selectively retains the intravascular device,
        a delivery catheter positioned longitudinally overlapping at least a portion of the coil, and
        a delivery disc longitudinally fixed to the delivery catheter, the delivery disc being proximal to the distal end cap; and
    a disc handle configured to move the distal end cap and delivery disc, the disc handle including:
        a main body distal end cap configured to move the distal end cap, and
        a movable body configured to move the delivery disc longitudinally relative to the distal end cap,
        wherein, the distal end cap is disposed on a disc handle side of the intravascular device positioned within the intravascular device cover in a pre-deployed configuration.

2. The system of claim 1, further comprising a distal cable configured to transmit tension from the main body to the distal end cap.

3. The system of claim 1, further comprising a proximal cable configured to transmit tension from the movable body to the distal end cap.

4. The system of claim 1, wherein the movable body is configured to be selectively fixed relative to the main body.

5. The system of claim 1, further comprising at least one tensioning element connected to the distal end cap or the delivery disc.

6. The system of claim 5, wherein the at least one tensioning element is a suture.

7. The system of claim 1, wherein the distal end cap or delivery disc further comprises a tensioning element release mechanism.

8. The system of claim 7, wherein the tensioning element release mechanism includes one or more electrically conductive elements.

9. An intravascular device delivery system, the system comprising:
- an elongated member having a distal end and a proximal end with a longitudinal axis extending therebetween, the elongated member including,
  - an outer sleeve,
  - at least one steerable catheter;
  - a coil positioned longitudinally overlapping and radially within at least a portion of the outer sleeve,
  - a distal end cap longitudinally fixed to the coil with the coil interfacing with the distal end cap from a proximal side of the distal end cap,
  - a delivery catheter positioned longitudinally overlapping and radially within at least a portion of the coil, and
  - a delivery disc longitudinally fixed to the delivery catheter and positioned within the coil;
- a disc handle configured to move the distal end cap and delivery disc, the disc handle including,
  - a main body configured to move the distal end cap longitudinally, and
  - a movable body configured to move the delivery disc longitudinally relative to the distal end cap; and
- an intravascular device positioned adjacent the distal end cap
- wherein, the distal end cap is disposed on a disc handle side of the intravascular device positioned within an intravascular device cover.

10. The system of claim 9, wherein the distal end cap is selectively longitudinally fixed to the outer sleeve.

11. The system of claim 9, wherein the intravascular device is connected to the delivery disc with at least one tensioning element.

12. The system of claim 9, wherein the distal end cap or delivery disc further comprises a tensioning element release mechanism.

13. The system of claim 12, wherein the tensioning element release mechanism includes one or more electrically conductive elements.

14. The system of claim 13, wherein the delivery catheter is configured to provide electrical communication to the tensioning element release mechanism.

15. The system of claim 9, further comprising at least one tensioning element connecting the outer sleeve to the disc handle.

16. An intravascular device delivery system for delivery of an intravascular device, the system comprising:
- an elongated member having a distal end and a proximal end with a longitudinal axis extending therebetween, the distal end configured to be inserted into a vasculature to deliver the intravascular device, the elongated member including:
  - an intravascular device cover having an intravascular device receiving cavity extending from a cover distal end toward a cover proximal end;
  - a flexible portion extending proximally from the cover proximal end;
  - a sealing member extending over the flexible portion; and
  - a swivel connection formed at the cover proximal end and a distal flexible portion end, the intravascular device cover and the flexible portion having a relationship in which the flexible portion is configured to swivel in relation to the intravascular device cover,
- wherein the intravascular device cover and the flexible portion are configured to be inserted into the vasculature to deliver the intravascular device.

17. The intravascular device delivery system of claim 16, wherein the flexible portion rotates about a longitudinal axis of the intravascular device cover.

18. The intravascular device delivery system of claim 17, wherein the intravascular device cover has a length approximating a length of the intravascular device.

19. The intravascular device delivery system of claim 16, wherein the flexible portion extends from the intravascular device cover to a location distal the proximal end of the elongated member.

20. The intravascular device delivery system of claim 16, wherein a first end of the sealing member is mounted to the flexible portion and a second end of the sealing member is mounted to a location proximal the flexible portion.

21. The intravascular device delivery system of claim 16, wherein an intermediate portion of the sealing member mounted to at least the flexible portion is freely movable relative to the flexible portion.

22. The intravascular device delivery system of claim 16, further comprising at least one steerable catheter.

23. The intravascular device delivery system of claim 16, further comprising a coil positioned longitudinally overlapping and radially within at least a portion of the flexible portion.

24. The intravascular device delivery system of claim 23, further comprising:
- a distal end cap longitudinally fixed to the coil,
- a catheter positioned longitudinally overlapping and radially within at least a portion of the coil, and
- a delivery disc longitudinally fixed to the catheter and positioned within the coil.

25. The intravascular device delivery system of claim 19, wherein a handle assembly further comprises a disc handle configured to move the distal end cap and a delivery disc, the disc handle comprising:
- a main body configured to move the distal end cap longitudinally, and
- a movable body configured to move the delivery disc longitudinally relative to a distal end cap.

* * * * *